(12) United States Patent
Inuzuka

(10) Patent No.: US 9,936,873 B2
(45) Date of Patent: Apr. 10, 2018

(54) OPTHALMOLOGY APPARATUS

(71) Applicant: Kabushiki Kaisha TOPCON, Tokyo (JP)

(72) Inventor: Naoki Inuzuka, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 45 days.

(21) Appl. No.: 15/102,634

(22) PCT Filed: Dec. 4, 2014

(86) PCT No.: PCT/JP2014/082160
§ 371 (c)(1),
(2) Date: Jun. 8, 2016

(87) PCT Pub. No.: WO2015/087784
PCT Pub. Date: Jun. 18, 2015

(65) Prior Publication Data
US 2016/0310003 A1    Oct. 27, 2016

(30) Foreign Application Priority Data
Dec. 13, 2013  (JP) .................................. 2013-258734

(51) Int. Cl.
*A61B 3/15* (2006.01)
*A61B 3/14* (2006.01)
(Continued)

(52) U.S. Cl.
CPC ............ *A61B 3/152* (2013.01); *A61B 3/0075* (2013.01); *A61B 3/10* (2013.01); *A61B 3/14* (2013.01); *A61B 3/15* (2013.01); *A61B 3/16* (2013.01)

(58) Field of Classification Search
CPC .......... A61B 3/0075; A61B 3/14; A61B 3/15; A61B 3/152; A61B 3/16; A61B 3/10
(Continued)

(56) References Cited

U.S. PATENT DOCUMENTS 4,364,646 A * 12/1982 Nohda .................... A61B 3/152
                                                             351/208
6,132,046 A * 10/2000 Iijima .................... A61B 3/152
                                                             351/208
(Continued)

FOREIGN PATENT DOCUMENTS

| CN | 101507601 A | 8/2009 |
| EP | 2 090 221 A1 | 8/2009 |

(Continued)

OTHER PUBLICATIONS

International Search Report issued in PCT/JP2014/082160; dated Jan. 13, 2015.

*Primary Examiner* — William R Alexander
(74) *Attorney, Agent, or Firm* — Studebaker & Brackett PC

(57) ABSTRACT

An ophthalmology apparatus includes an apparatus body on which a first measurer and a second measurer are provided and which is movable relative to a base by a driver, a forehead support provided on the base, and a controller. The controller detects a first front position setting a distance between the second measurer and the forehead support as a first interval and a second front position setting a distance between the second measurer and the forehead support as a second interval larger than the first interval, and emits a warning when the apparatus body reaches the second front position in moving the apparatus body to a forehead support side and stops movement of the apparatus body to the forehead support side when the apparatus body reaches the first front position.

12 Claims, 10 Drawing Sheets

(51) Int. Cl.
*A61B 3/10* (2006.01)
*A61B 3/16* (2006.01)
*A61B 3/00* (2006.01)

(58) Field of Classification Search
USPC .......................................................... 351/208
See application file for complete search history.

(56) References Cited

U.S. PATENT DOCUMENTS

| | | | |
|---|---|---|---|
| 7,909,462 B2 * | 3/2011 | Takahashi | A61B 3/0083 351/208 |
| 2004/0008322 A1 * | 1/2004 | Ogawa | A61B 3/107 351/208 |
| 2009/0207378 A1 | 8/2009 | Ito et al. | |
| 2012/0220850 A1 * | 8/2012 | Umekawa | A61B 3/0041 600/401 |
| 2013/0258286 A1 * | 10/2013 | Iwase | A61B 3/0041 351/208 |
| 2013/0293837 A1 * | 11/2013 | Akiba | A61B 3/18 351/205 |
| 2014/0358039 A1 * | 12/2014 | Pearson | A61B 3/10 600/587 |
| 2017/0196448 A1 * | 7/2017 | Pearson | A61B 3/101 |

FOREIGN PATENT DOCUMENTS

| | | |
|---|---|---|
| JP | 2002-253506 A | 9/2002 |
| JP | 2007-282672 A | 11/2007 |
| JP | 2009-189624 A | 8/2009 |
| JP | 2010-148589 A | 7/2010 |
| JP | 2012-170590 A | 9/2012 |
| KR | 10-2009-0088822 A | 8/2009 |

* cited by examiner

FIG.7A
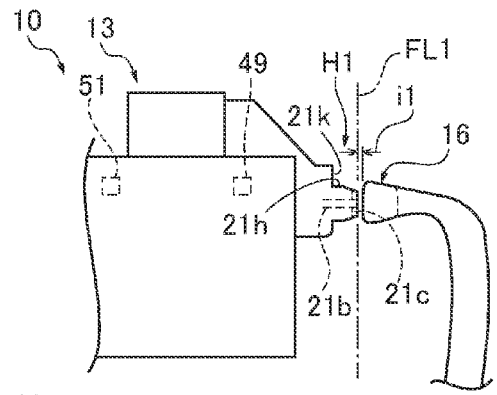
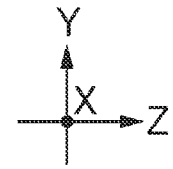
FIG.7B
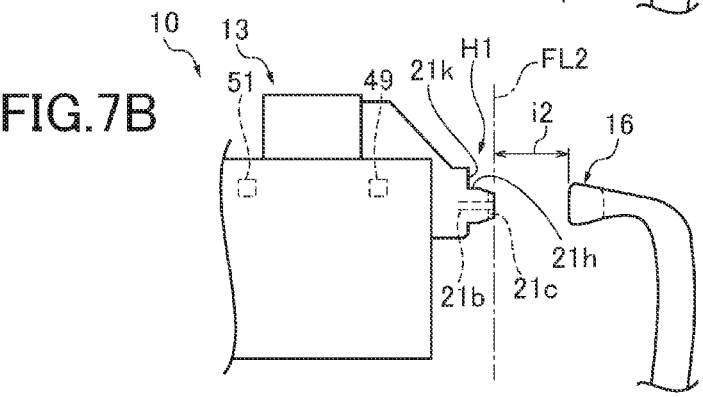
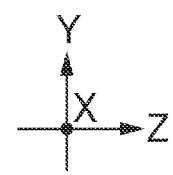
FIG.7C
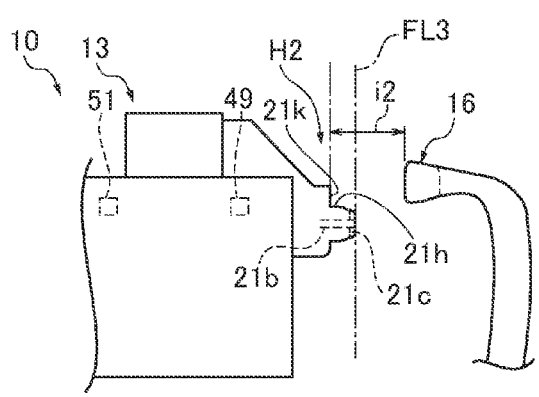
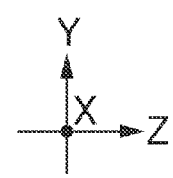
FIG.7D
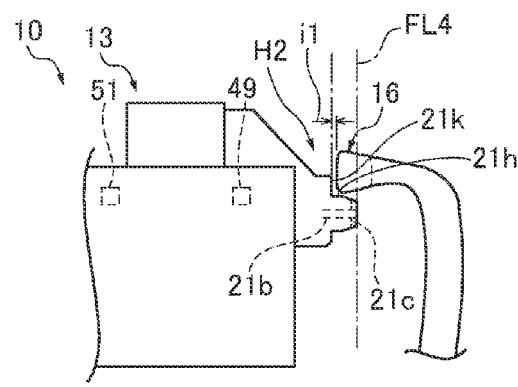
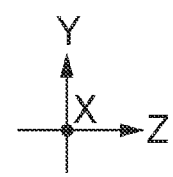

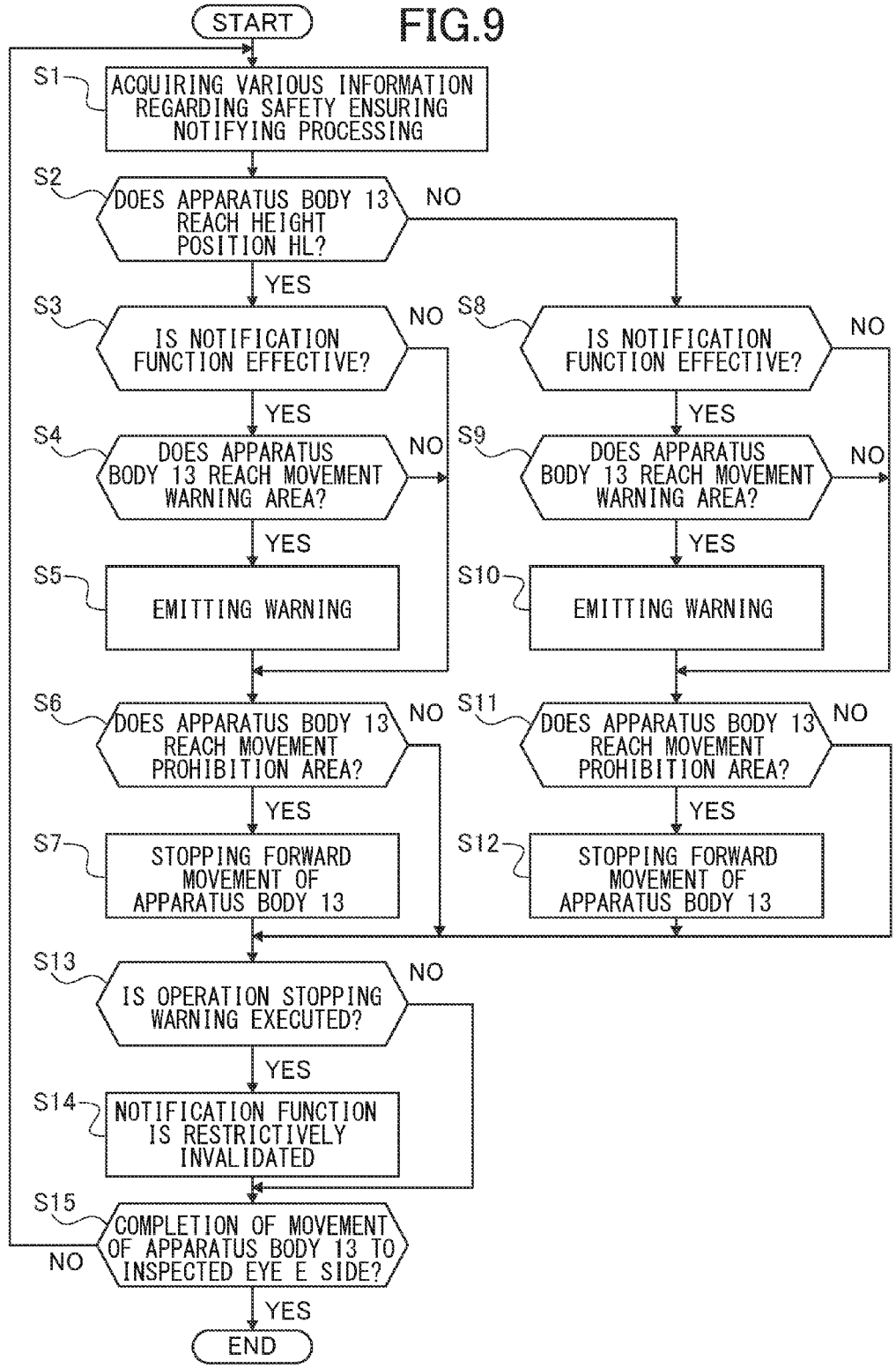

OPTHALMOLOGY APPARATUS

CROSS-REFERENCE TO RELATED APPLICATION

This application is based upon and claims the benefit of priority to Japanese Patent Application No. 2013-258734, filed on Dec. 13, 2013, the entire disclosures of which are incorporated herein by reference.

TECHNICAL FIELD

The present invention relates to a compound-type ophthalmology apparatus including a first measurer set at a first setting working distance and a second measurer set at a second setting working distance.

BACKGROUND ART

A compound-type ophthalmology apparatus including a first measurer set at a first setting working distance and a second measurer set at a second setting working distance shorter than the first setting working distance is proposed (for example, Patent Literature 1). The ophthalmology apparatus includes an intraocular pressure measurement device as the second measurer in which the second setting working distance has a very small value and a separate eye characteristic measurement device as the first measurer in which the first setting working distance has a relatively large value. In the ophthalmology apparatus, various measurements are executed by fitting a forehead of the subject to a forehead support to fix the face, that is, an inspected eye of the subject and by moving the first measurer or the second measurer to a position where measurement is adequately executed.

Here, in the compound-type ophthalmology apparatus as described above, there is an apparatus having a configuration in which the second measurer is integrally provided above the first measurer and the first measurer and the second measurer can be moved while maintaining a positional relationship therebetween. In such a compound-type ophthalmology apparatus, it is considered that the second measurer is configured to locate in front of the first measurer, that is, protrude to a subject side. This is because the arrangement makes it possible to prevent the first measurer from being in contact with the nose or mouth of the subject, or from giving an obstructive feeling to the subject even if there is no contact, when measuring the inspected eye by use of the second measurer which is upward positioned.

CITATION LIST

Patent Literature

Patent Literature 1: JP2010-148589A

SUMMARY

Technical Problem

However, in the compound-type ophthalmology apparatus, when forward moving the first measurer in measuring the inspected eye by use of the first measurer which is downward positioned, the second measurer (tip thereof) which is upward and forward positioned approaches the forehead support which is positioned above the inspected eye. There is a problem that the second measurer (tip thereof) therefore interferes with the forehead support depending on a positional setting or quantity of movement, or the hand of the subject is interposed between the second measurer and the forehead support in a case where the hand is put on the forehead support even if there is no interference.

The present invention is made to solve the above problem, and it is an object of the present invention to provide an ophthalmology apparatus capable of preventing a second measurer from interfering with a forehead support and the hand put on the forehead support from being interposed between the second measurer and the forehead support.

Solution to Problem

To solve the above problem, an ophthalmology apparatus according to claim 1 includes a first measurer set at a first setting working distance to measure an inspected eye of a subject, a second measurer set at a second setting working distance shorter than the first setting working distance to measure the inspected eye and integrally provided above the first measurer, an apparatus body on which the first measurer and the second measurer are provided and which is movable relative to a base, a driver that moves the apparatus body relative to the base, a forehead support provided on the base to support a forehead of the subject, and a controller that controls the first measurer, the second measurer, and the driver. The controller is configured to detect a first front position in the apparatus body, in which a distance between the second measurer and the forehead support is set as a first interval and a second front position in the apparatus body, in which a distance between the second measurer and the forehead support is set as a second interval larger than the first interval. The controller emits a warning when the apparatus body reaches the second front position in moving the apparatus body to a forehead support side and stops the movement of the apparatus body to the forehead support side when the apparatus body reaches the first front position.

Advantageous Effects

According to the ophthalmology apparatus according to the present invention, the second measurer is prevented from interfering with the forehead support, and the hand put on the forehead support can be prevented from being interposed between the second measurer and the forehead support.

BRIEF DESCRIPTION OF DRAWINGS

FIG. 7A is an explanatory view showing a first front position of a nozzle projection.

FIG. 7B is an explanatory view showing a second front position of the nozzle projection.

FIG. 7C is an explanatory view showing a third front position of the nozzle projection.

FIG. 7D is an explanatory view showing a fourth front position of the nozzle projection.

FIG. 9 is a flow chart showing safety ensuring notifying processing (method of notifying safety ensuring) executed by a controller 33 in the embodiment.

DETAILED DESCRIPTION OF EMBODIMENTS

Embodiments of an ophthalmology apparatus according to the present invention will be described hereinafter with reference to the accompanying drawings.

Figure 3:
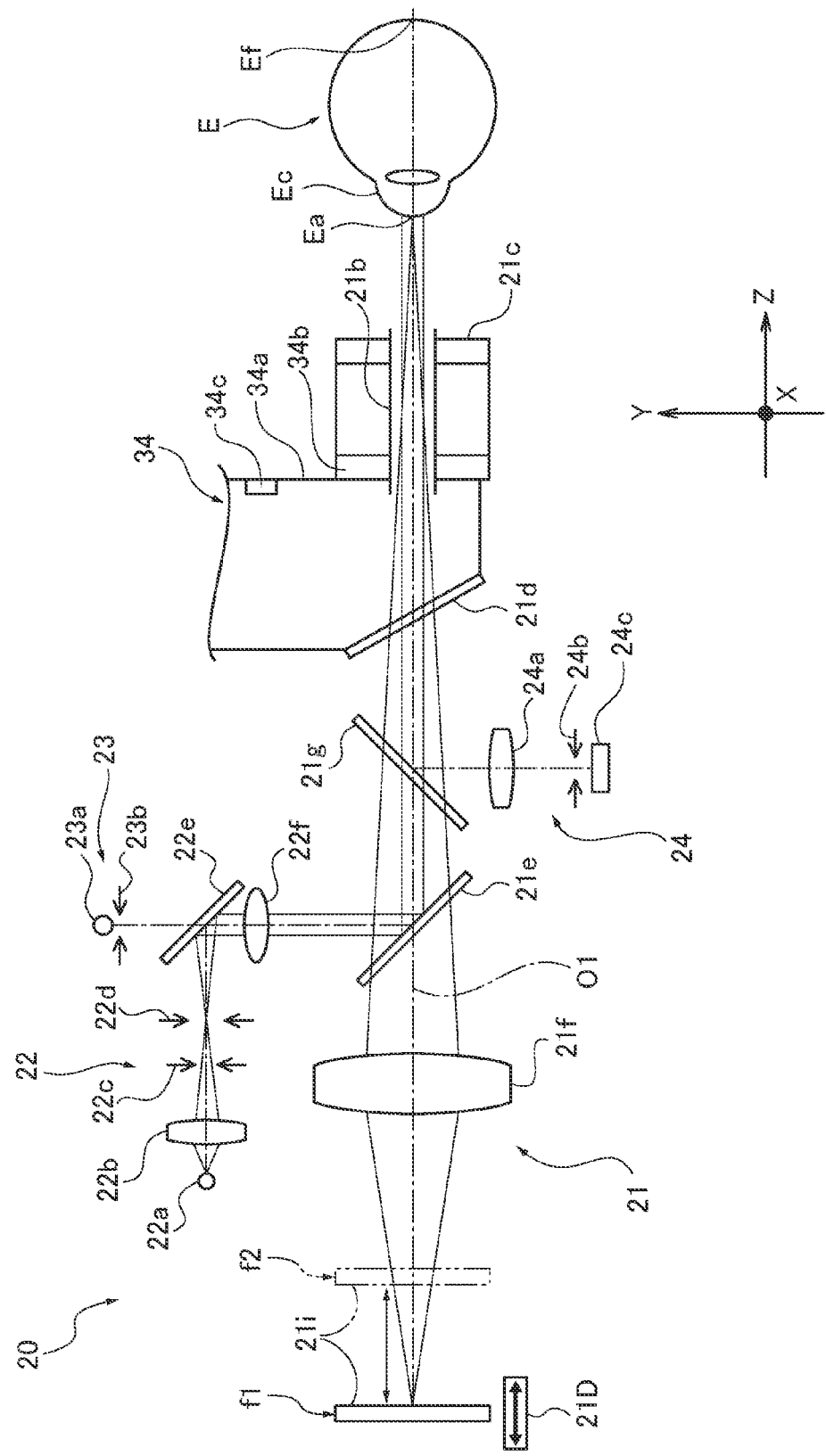
FIG. 3 is an explanatory view as viewed from a different direction from FIG. 2 for explaining the optical configuration of the intraocular pressure measurement device 20 of the ophthalmology apparatus 10.
Figure 4:
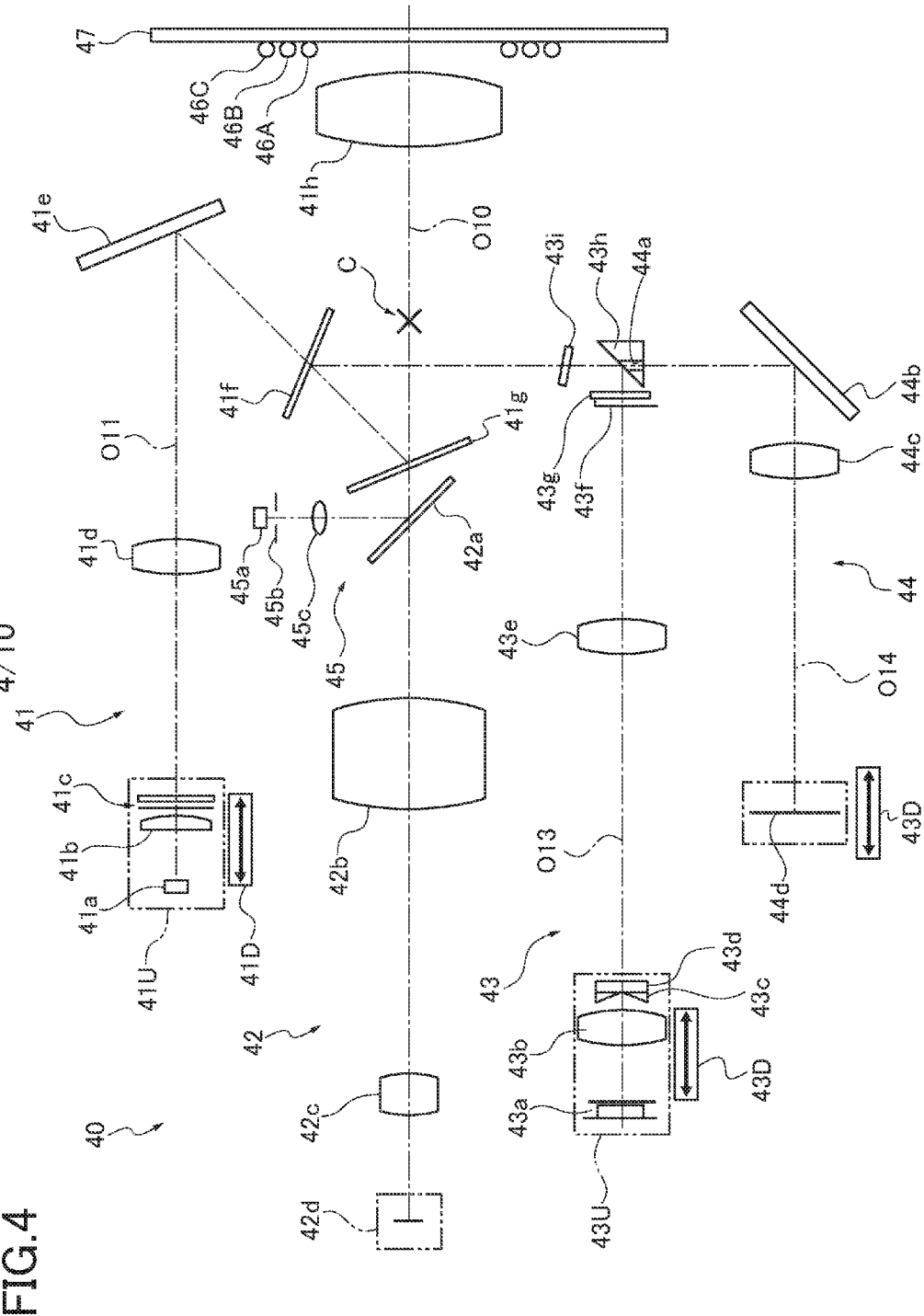
FIG. 4 is an explanatory view for explaining an optical configuration of an eye characteristic measurement device 40 of the ophthalmology apparatus 10.
Figure 5A:
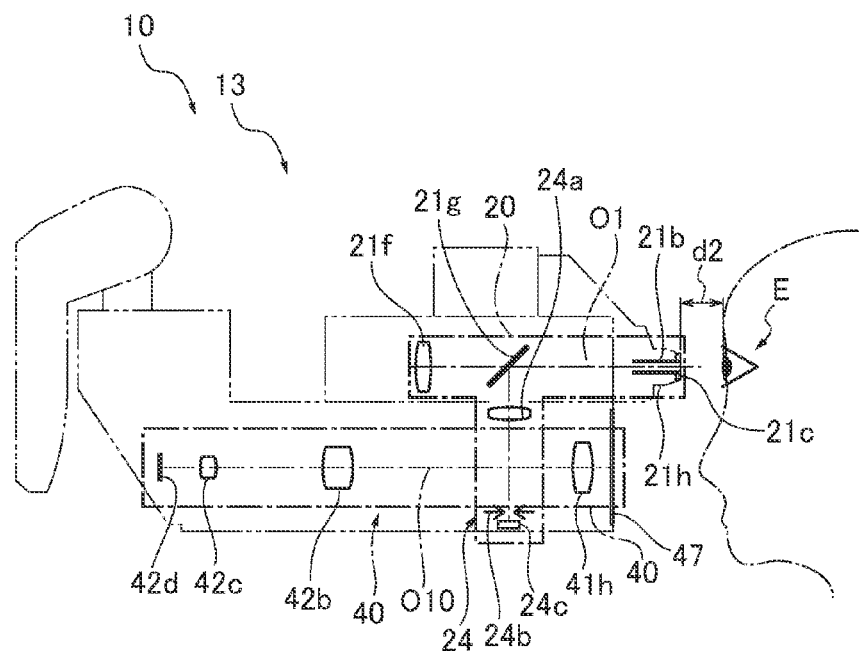
FIG. 5A is an explanatory view showing an intraocular pressure measurement mode.
Figure 5B:
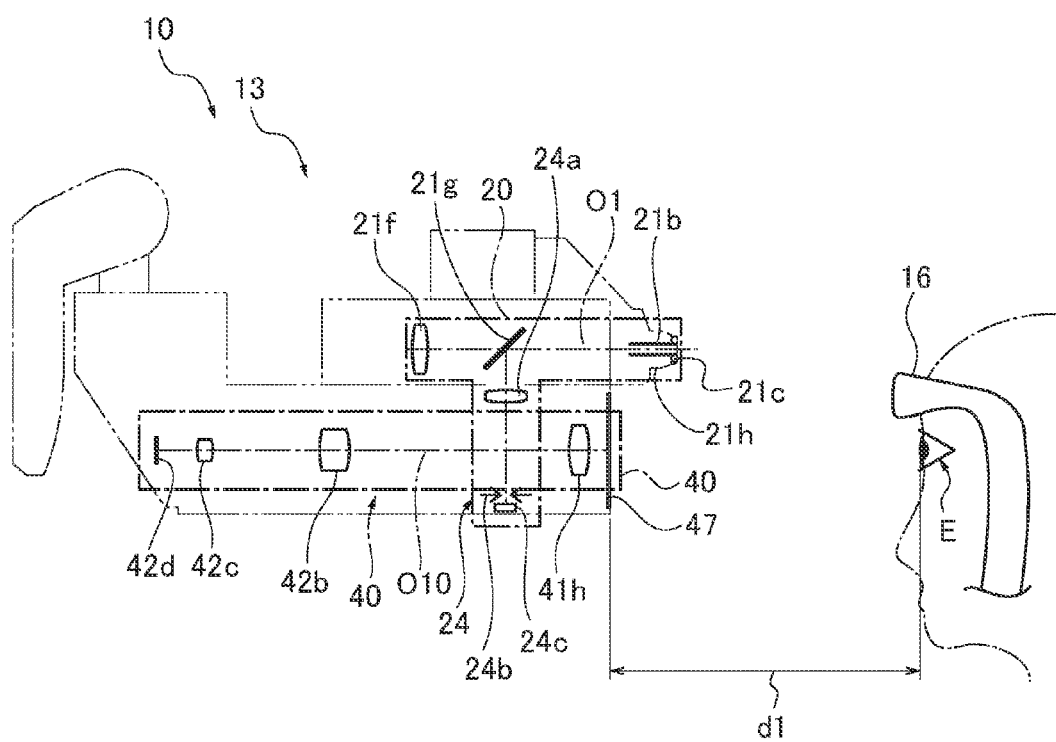
FIG. 5B is an explanatory view showing an eye characteristic measurement mode.
Figure 10A:
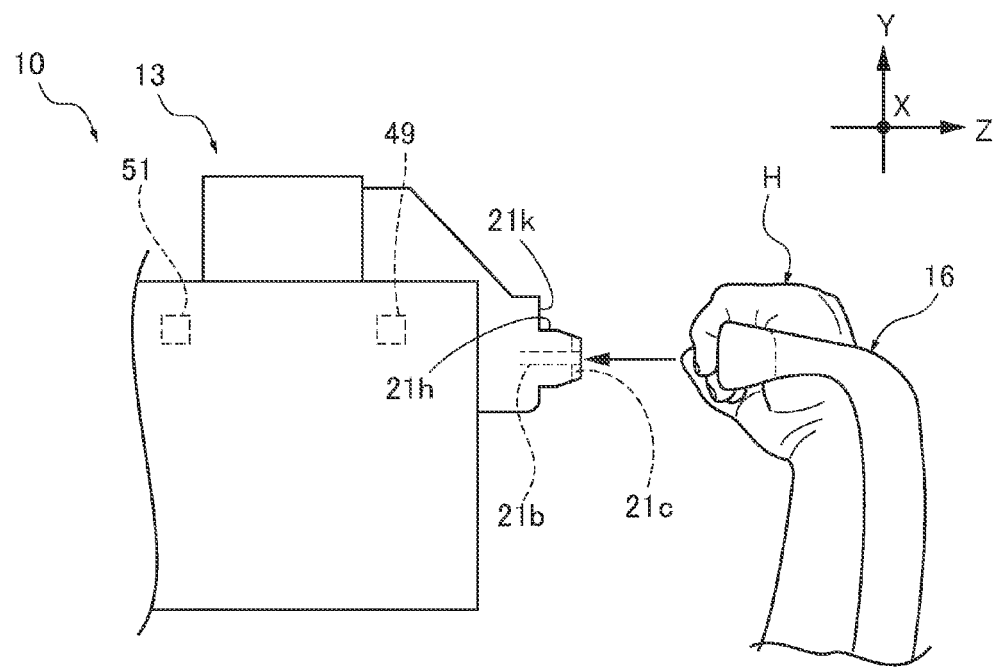
FIG. 10A is an explanatory view showing a state where a hand is placed on a forehead support.
Figure 10B:
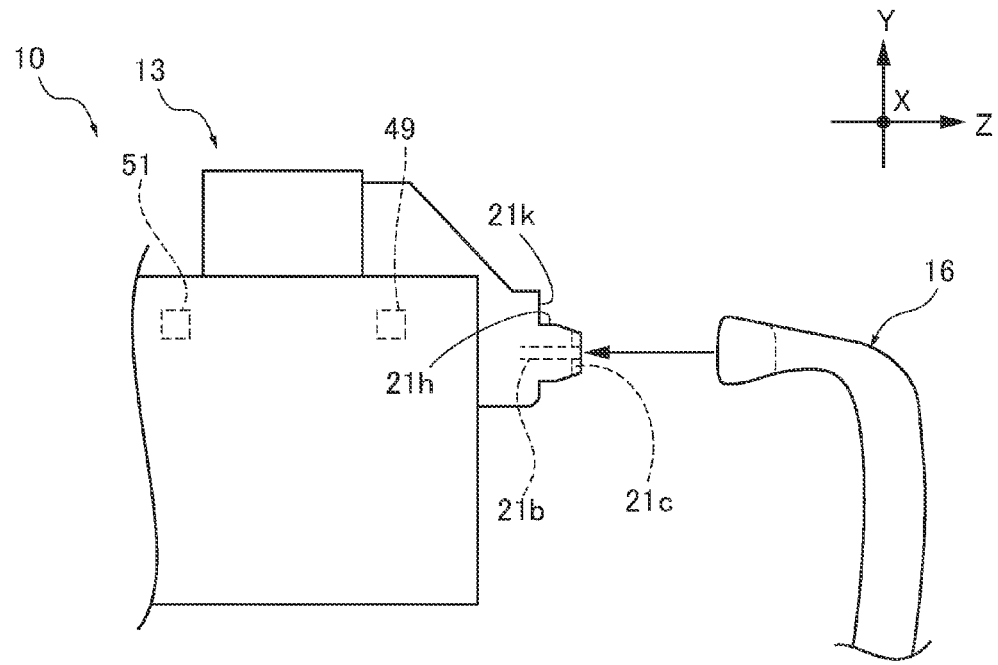
FIG. 10B is an explanatory view showing a state where the hand is not placed on the forehead support.

The ophthalmology apparatus 10 as one embodiment of the present invention is described with reference to FIGS. 1 to 10. Here, FIG. 5A illustrates an intraocular pressure measurement mode, and FIG. 5B illustrates an eye characteristic measurement mode. FIG. 7A illustrates a first front position FL1, FIG. 7B illustrates a second front position FL2, FIG. 7C illustrates a third front position FL3, and FIG. 7D illustrates a fourth front position FL4. FIG. 10A illustrates a state where a hand is placed on a forehead support 16, and FIG. 10B illustrates a state where the hand is not placed on the forehead support 16.

Figure 1:
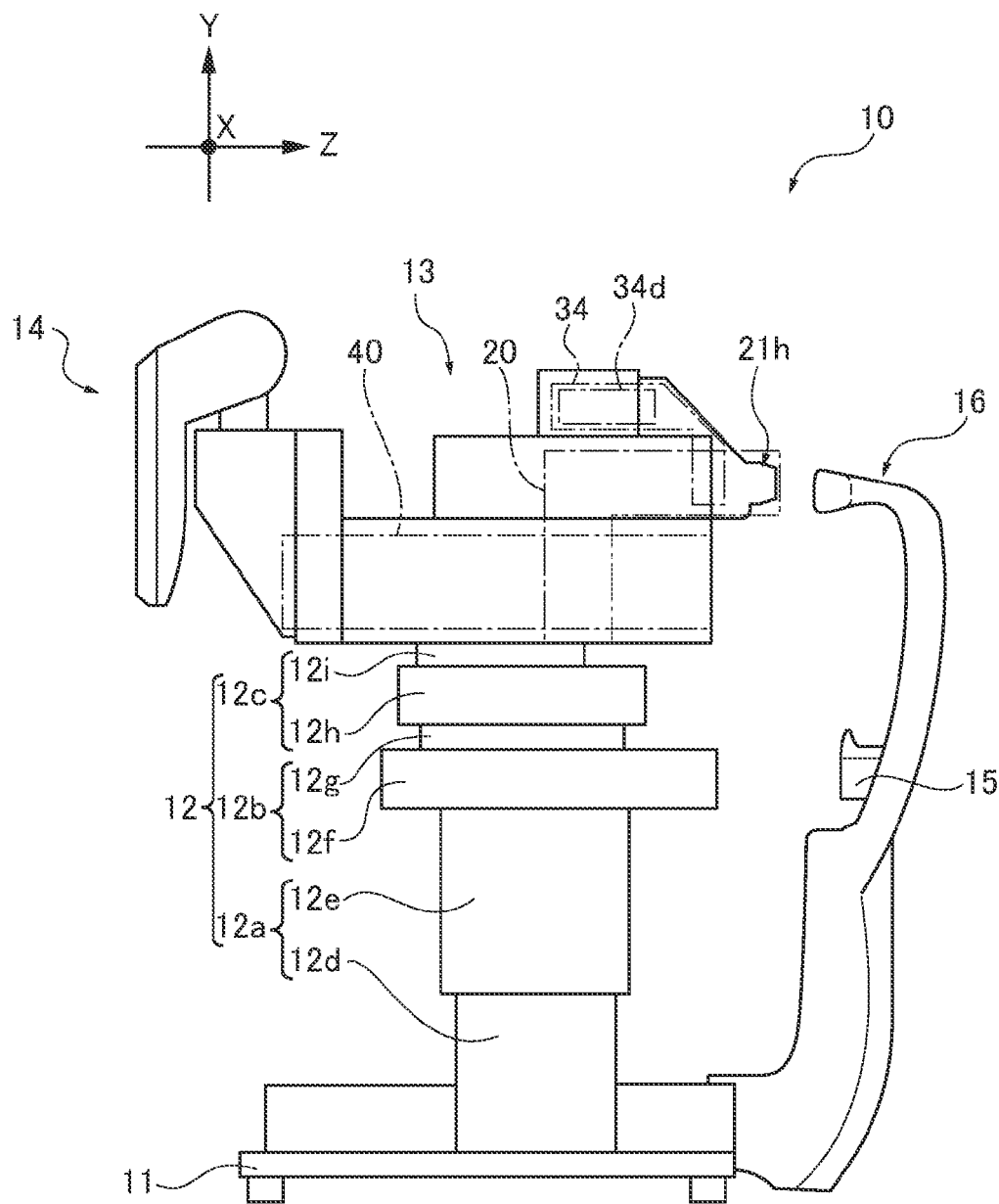
FIG. 1 is an explanatory view schematically showing an optical configuration of an ophthalmology apparatus 10 in an embodiment according to the present invention.
Figure 2:
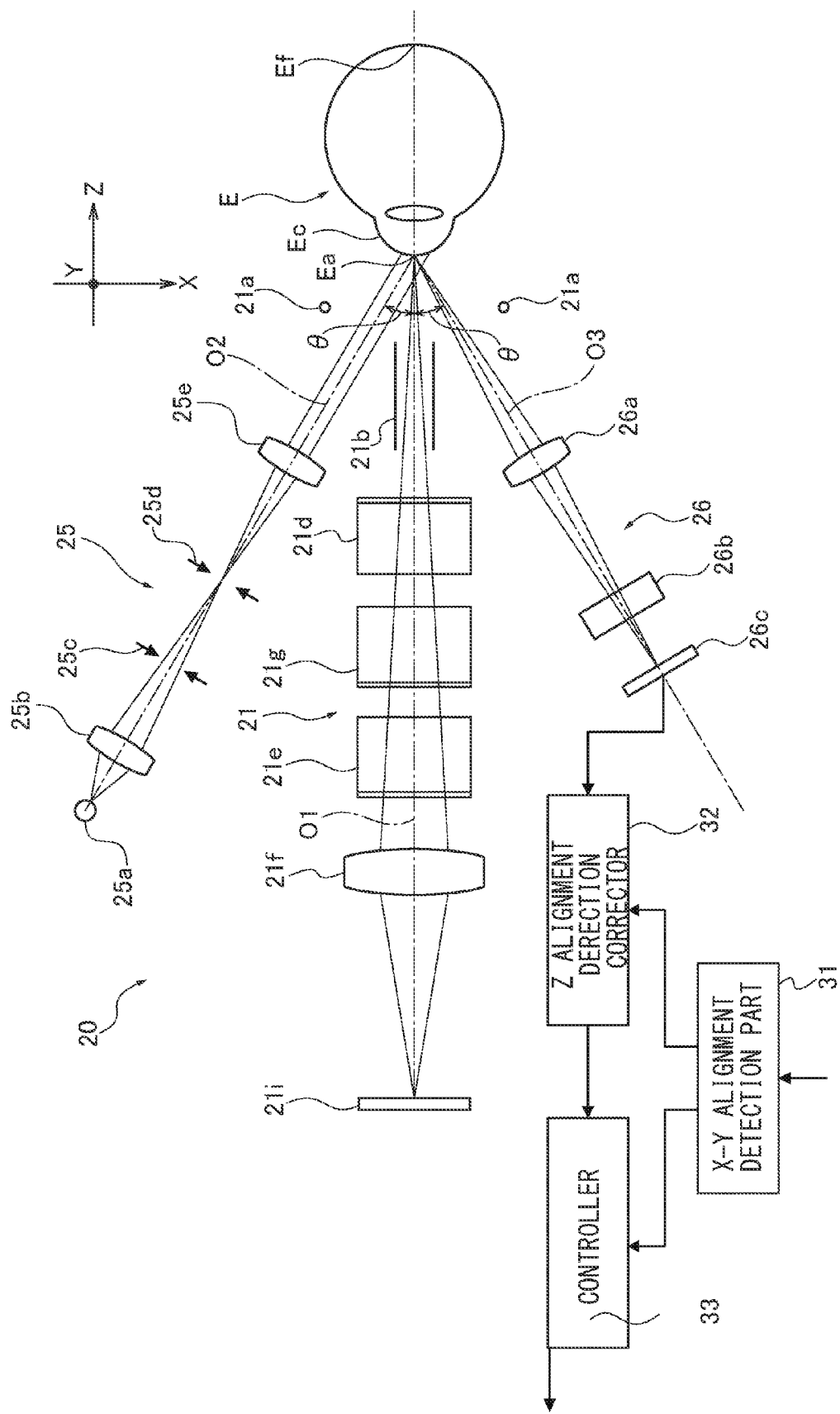
FIG. 2 is an explanatory view for explaining an optical configuration of an intraocular pressure measurement device 20 in the ophthalmology apparatus 10.

The ophthalmology apparatus 10 is a compound-type ophthalmology apparatus including an intraocular pressure measurement device 20 that measures an intraocular pressure of an inspected eye E (see FIG. 2 and so on) as one example of a second measurer and an eye characteristic measurement device 40 that measures other optical characteristics (eye characteristics) of the inspected eye E as a first measurer, as shown in FIG. 1. An eye ground (retina) Ef, a cornea (anterior ocular segment) Ec, and an apex of the cornea Ea of the inspected eye E are illustrated in FIGS. 2 and 3. The ophthalmology apparatus 10 is composed of an apparatus body 13 which is provided on a base 11 through a driver 12. The intraocular pressure measurement device 20 and the eye characteristic measurement device 40 are provided inside the apparatus body 13, and a display 14, a jaw rest 15, and the forehead support 16 are provided outside the apparatus body.

The display 14 is formed by a liquid crystal display and displays an image such as an image of the anterior ocular segment, an inspection result and so on of the inspected eye E under control of a controller 33 (see FIG. 2) as described below. The display 14 installs a function of touch panel in the present embodiment and is configured to be capable of executing operation to measure the inspected eye by using the intraocular pressure measurement device 20 and the eye characteristic measurement device 40, or executing operation to move the apparatus body 13 by manual operation. In addition, the display 14 displays a switching icon in each measurement mode as described above by using the function of touch panel and can execute switching operation of each measurement mode by touching the switching icon. Note that operation to execute the measurement may be executed by operation of a measurement switch by providing the measurement switch. Operation to move the apparatus body 13 may be executed by a control lever or movement operation switch by providing the control lever or the movement operation switch.

The jaw rest 15 and the forehead support 16 hold a face of a subject (patient), in other words, the position of the inspected eye E to the apparatus body 13 when measuring, and are fixedly provided on the base 11. The jaw rest 15 is a part where the subject places the jaw thereon and the forehead support 16 is a part where the subject applies the forehead thereto. In the ophthalmology apparatus 10, the display 14, and the jaw rest 15 and the forehead support 16 are arranged at both sides of the apparatus body 13 to face each other across the apparatus body 13. In a usual use state of the ophthalmology apparatus 10, the display 14 is disposed at a side of an examiner and the jaw rest 15 and the forehead support 16 are disposed at a side of the subject. The display 14 is rotatably supported on the apparatus body 13 to be capable of changing a direction of a display surface, for example, to direct the display surface to the subject or to direct the display surface to a side (an X-axis direction). The apparatus body 13 is movable relative to the base 11, that is, the inspected eye E (the face of the subject) fixed by the jaw rest 15 and the forehead support 16 by the driver 12.

The driver 12 moves the apparatus body 13 relative to the base 11 in an up-down direction (a Y-axis direction), a front-back direction (a Z-axis direction (right-left direction as viewed FIG. 1 in front)), and a right-left direction (the X-axis direction (a perpendicular direction to a paper plane in FIG. 1)) perpendicular thereto. Note that, in the embodiment, an upper side in the up-down direction is defined as a positive side in the Y-axis direction, a side of the subject (a right side as viewed FIG. 1 in front) in the front-back direction is defined as a positive side in the Z-axis direction, and a near side as viewed in FIG. 1 in front in the right-left direction is defined as a positive side in the X-axis direction (see arrows in FIG. 1). In the embodiment, the driver 12 includes a Y-axis driving part 12a, a Z-axis driving part 12b, and an X-axis driving part 12c.

The Y-axis driving part 12a is provided on the base 11 and moves (displays) the apparatus body 13 relative to the base 11 in the Y-axis direction (up-down direction) through the Z-axis driving part 12b, and the X-axis driving part 12c. In other words, the Y-axis driving part 12a is a part that moves the apparatus body 13 in the Y-axis direction (up-down direction), in the driver 12. The Y-axis driving part 12a has a supporting column 12d and a Y-axis moving frame 12e. The supporting column 12d is fixedly provided on the base 11 and is configured to extend from the base 11 in the Y-axis direction. The Y-axis moving frame 12e is configured to be capable of surrounding the supporting column 12d and attached to the supporting column 12d to be relatively movable in the Y-axis direction through a Y-axis guide member which is not shown. The Y-axis moving frame 12e is set such that a movable range relative to the supporting column 12d (base 11) in the Y-axis direction can position the intraocular pressure measurement device 20 at the lowermost position (negative side) in an intraocular pressure measurement mode as described below (see FIG. 5A) and the eye characteristic measurement device 40 at the uppermost position (positive side) in an eye characteristic measurement mode as described below (see FIG. 5B).

A resilient member which is not shown is provided between the Y-axis moving frame 12e and the supporting column 12d and is configured to impart a force pressing upwardly the Y-axis moving frame 12e. The resilient member is composed of a tension spring which is formed by a spirally wound wire material in the embodiment. The tension spring is configured to be contracted most in an unloaded state and generates a resilient force against operation in which one end and another end separate from each other. In other words, the Y-axis moving frame 12e is configured to be suspended with respect to the supporting column 12d by the resilient member. The Y-axis moving frame 12e is supported on the supporting column 12d (base 11) through the resilient member in a state where a relative moving direction of the Y-axis moving frame 12e to the supporting column 12d (base 11) by the Y-axis guide member is defined in the Y-axis direction. Note that the resilient member may use a compression spring or other configuration and is not limited to the embodiment, as long as the Y-axis moving frame 12e is supported by imparting to the Y-axis moving frame 12e a force pressing the Y-axis moving frame 12e to the supporting column 12d (base 11) in the Y-axis direction. In this case, the compression spring is formed by a spirally wound wire material and configured to be extended most in an unloaded state and generates a resilient force against operation in which one end and another end are close to each other. In the case using the compression spring, the supporting column 12d or the base 11 may be configured to support the Y-axis moving frame 12e from below through the compression spring.

A drive-force transmission mechanism that transmits a drive force to move the Y-axis moving frame 12e relative to the supporting column 12d in the Y-axis direction is provided on the Y-axis driving part 12a. In the Y-axis driving part 12a, the Y-axis moving frame 12e is moved from a balanced position of the resilient member to the positive side of the Y-axis direction by imparting an upward moving force from the drive-force transmission mechanism to the Y-axis moving frame 12e, and the Y-axis moving frame 12e is moved from the balanced position of the resilient member to the negative side of the Y-axis direction by imparting a downward moving force from the drive-force transmission mechanism to the Y-axis moving frame 12e.

The Z-axis driving part 12b is provided on the Y-axis moving frame 12e (the Y-axis driving part 12a) and moves (displaces) the apparatus body 13 relative to the Y-axis driving part 12a, that is, the base 11 in the Z-axis direction (front-back direction) through the X-axis driving part 12c. In other words, the Z-axis driving part 12b is a part for moving the apparatus body 13 in the Z-axis direction (front-back direction) in the driver 12. The Z-axis driving part 12b includes a Z-axis supporting stage 12f and a Z-axis movable table 12g. The Z-axis supporting stage 12f is fixedly provided on the Y-axis moving frame 12e and moved together with Y-axis moving frame 12e in the Y-axis direction. The Z-axis supporting stage 12f supports the Z-axis movable table 12g to be relatively movable in the Z-axis direction through a Z-axis guide member which is not shown. The Z-axis driving part 12b is provided with a drive-force transmission mechanism that imparts a drive force to move the Z-axis movable table 12g relative to the Z-axis supporting stage 12f in the Z-axis direction. In the Z-axis driving part 12b, the Z-axis movable table 12g is suitably moved in the Z-axis direction by imparting the drive force from the drive-force transmission mechanism to the Z-axis movable table 12g.

The X-axis driving part 12c is provided on the Z-axis movable table 12g (the Z-axis driving part 12b) and moves (displaces) the apparatus body 13 relative to the Z-axis driving part 12b, that is, the base 11 in the X-axis direction (right-left direction). In other words, the X-axis driving part 12c is a configuration that moves the apparatus body 13 in the X-axis direction (right-left direction) in the driver 12. The X-axis driving part 12c includes an X-axis supporting stage 12h and an X-axis movable table 12i. The X-axis supporting stage 12h is fixedly provided on the Z-axis movable table 12g and is moved together with the Z-axis movable table 12g in the Z-axis direction. The X-axis supporting stage 12h supports the X-axis movable table 12i to be relatively movable in the X-axis direction though an X-axis guide member which is not shown. The X-axis driving part 12c is provided with a drive-force transmission mechanism that imparts a drive force to move the X-axis movable table 12i relative to the X-axis supporting stage 12h in the X-axis direction. In the X-axis driving part 12c, the X-axis movable table 12i is suitably moved in the X-axis direction by imparting the drive force in the X-axis direction from the drive-force transmission mechanism to the X-axis movable table 12i. The apparatus body 13 is fixed to the X-axis movable table 12i through a mounting substrate (not shown) to which the intraocular pressure measurement device 20 and the eye characteristic measurement device 40 provided inside the apparatus body 13 are attached.

It is therefore possible to suitably move the apparatus body 13 relative to the base 11 in the up-down direction (Y-axis direction), the front-back direction (Z-axis direction), and the right-left direction (X-axis direction) by suitably driving the Y-axis driving part 12a, the Z-axis driving part 12b, and the X-axis driving part 12c in the driver 12. Note that, in the driver 12, the Y-axis driving part 12a, the Z-axis driving part 12b, and the X-axis driving part 12c are connected to the controller 33 (see FIG. 2), although it is not specifically shown, thereby each driving part is driven under control of the controller 33. The controller 33 configures an electric control system for the ophthalmology apparatus 10 and generally controls each part of the ophthalmology apparatus 10 by a program stored in a built-in memory.

In FIG. 1, the ophthalmology apparatus 10 is provided with a cover member that forms the entire outer shape of the ophthalmology apparatus. The cover member is omitted to facilitate understanding and covers the ophthalmology apparatus 10 over a range from the base 11 through the driver 12 to apparatus body 13. In addition, FIG. 1 illustrates the Y-axis driving part 12a, the Z-axis driving part 12b, and the X-axis driving part 12c in the driver 12 to be stacked in the Y-axis direction, but they are not completely divided in the Y-axis direction. Each driving part is configured to be overlapped when viewing in a direction perpendicular to the Y-axis direction. It is therefore possible for the driver 12, that is, the ophthalmology apparatus 10 to prevent a height dimension (dimension as viewed in the Y-axis direction) from increasing and to suitably move the apparatus body 13 relative to the base 11.

The apparatus body 13 is provided with the intraocular pressure measurement device 20 and the eye characteristic measurement device 40 disposed therein. The eye characteristic measurement device 40 constitutes a first measurer set at a first setting working distance d1 (see FIG. 5B), and the intraocular pressure measurement device 20 constitutes a second measurer set at a second setting working distance d2 (see FIG. 5A) shorter than the first setting working distance. Each working distance is a distance capable of executing measurement of the inspected eye E by each measurer and is shown by a distance (interval) from a tip of each measurer to the inspected eye E. The intraocular pressure measurement device 20 is used in measuring the intraocular pressure of the inspected eye E. The eye characteristic measurement device 40 measures the optical characteristic (eye characteristic). In the embodiment, the eye characteristic measurement device is used in measuring a shape of the cornea Ec of the inspected eye E and refractive power (spherical power, astigmatic power, an astigmatic axis angle, and so on) of the inspected eye E.

In the ophthalmology apparatus 10 in the embodiment, an optical axis O1 as described below, which is a main optical axis of the intraocular pressure measurement device 20 in the apparatus body 13, is disposed to be upper (positive side in the Y-axis direction) than a main optical axis O1O as described below in the eye characteristic measurement device 40 (see FIGS. 5A and 5B). Therefore, in the ophthalmology apparatus 10, basically the intraocular pressure measurement device 20 is provided above the eye characteristic measurement device 40 in the apparatus body 13. Here, a reason referred to as "basically" with respect to a positional relationship between the intraocular pressure measurement device 20 and the eye characteristic measurement device 40 is for forming an integral structure configured to match parts of the intraocular pressure measurement device 20 and the eye characteristic measurement device 40 by intersecting a part of one optical system with another optical system in the intraocular pressure measurement device 20 and the eye characteristic measurement device 40, without they being individually separated.

Next, an optical configuration of the intraocular pressure measurement device 20 is described with reference to FIGS. 2 and 3. The intraocular pressure measurement device 20 is a non-contact type tonometer. The intraocular pressure measurement device 20 includes an anterior ocular segment observing optical system 21 as one example of an observation optical system, an X-Y alignment index projecting optical system 22, a fixation target projecting optical system 23, an applanation detecting optical system 24, a Z alignment index projecting optical system 25 as one example of a detection optical system, and a Z alignment detecting optical system 26 as one example of the detection optical system, as shown in FIGS. 2 and 3.

The anterior ocular segment observing optical system 21 is provided to execute the observation of the anterior ocular segment of the inspected eye E and X-Y alignment (alignment in a direction along an X-Y plane). The anterior ocular segment observing optical system 21 is provided with anterior ocular segment illuminating light sources 21a (see FIG. 2) and includes an air flow blowing nozzle 21b, an anterior ocular segment window glass 21c (see FIG. 3), a chamber window glass 21d, a half mirror 21e, a half mirror 21g, an object lens 21f, and a CCD camera 21i, which are arranged on an optical axis O1. The plurality of anterior ocular segment illuminating light sources 21a is arranged around the anterior ocular segment window glass 21c (see FIG. 2) (only two light sources are shown in FIG. 2) and configured to illuminate the anterior ocular segment directly. The air flow blowing nozzle 21b is a nozzle to brow air flow to the inspected eye E (the anterior ocular segment) and is provided in an air compression chamber 34a of an air flow blowing mechanism 34 which is described below (see FIG. 3). The CCD camera 21i generates an image signal based on an image (image of the anterior ocular segment and so on) formed on a light-receiving surface, and the generated image signal is output to the controller 33 (see FIG. 2). The image acquired by the CCD camera 21i is suitably displayed on the display 14 (see FIG. 1) under control of the controller 33 and suitably output to an external device which is not shown.

The CCD camera 21i is configured to be movable along the optical axis O1 by a focusing drive mechanism 21D, as shown in FIG. 3. The focusing drive mechanism suitably moves the CCD camera 21i to focus on the anterior ocular segment (cornea Ec) of the inspected eye E under control of the controller 33 (see FIG. 2). The focusing drive mechanism 21D has a drive source using together with that of a fixation target moving mechanism 41D (see FIG. 4) of a fixation target projecting optical system 41 as described below. That is to say, the drive source drives the focusing drive mechanism 21D in an intraocular pressure measurement mode (see FIG. 5A) described below and drives the fixation target moving mechanism 41D in an eye characteristic measurement mode (see FIG. 5B) described below. The controller 33 focuses the CCD camera 21i on the anterior ocular segment (cornea Ec) of the inspected eye E by changing a position of the CCD camera on the optical axis O1 in accordance with a position of the intraocular pressure measurement device 20, that is, the apparatus body 13 through the focusing drive mechanism 21D.

In the embodiment, the controller 33 can move the CCD camera 21i through the focusing drive mechanism 21D at two positions of a first focusing position f1 and a second focusing position f2 on the optical axis O1. The movement of the CCD camera 21i through the focusing drive mechanism 21D may be switched to two steps in the first focusing position f1 and the second focusing position f2 or continuously moved between the first focusing position f1 and the second focusing position f2.

The first focusing position f1 is a position focusing on a vicinity of the anterior ocular segment (cornea Ec) of the inspected eye E when setting the intraocular pressure measurement device 20 (apparatus body 13) to a position where the measurement of the intraocular pressure of the inspected eye E can be executed, in other words, from the anterior ocular segment (cornea Ec) of the inspected eye E to the second setting working distance d2 (see FIG. 5A). The position where the measurement of the intraocular pressure of the inspected eye E can be executed is set to be a distance (interval) from the tip of the air flow blowing nozzle 21b (a nozzle projection 21h described below) to the inspected eye E, that is a position where the second setting working distance d2 is set to be 11 mm (see FIG. 5A), in the embodiment.

The second focusing position f2 is a position focusing on a vicinity of the anterior ocular segment (cornea Ec) of the inspected eye E when setting the intraocular pressure measurement device 20 (apparatus body 13) to a position sufficiently separated from the inspected eye E (subject). This is because the intraocular pressure measurement device 20 (apparatus body 13) is first moved in the Y-axis direction to be set to a height position facing the inspected eye E and then moved in the Z-axis direction to approach the inspected eye E, when switching from the eye characteristic measurement mode (measurement mode by the eye characteristic measurement device 40) to the intraocular pressure measurement mode (measurement mode by the intraocular pressure measurement device 20), as described below. This movement is executed to prevent the air flow blowing nozzle 21b (the nozzle projection 21h described below, (the tip thereof)) very nearing the inspected eye E from coming in contact with the inspected eye E erroneously. Or, when switching the inspected eye E which is a measured object by right and left eyes of the subject in the intraocular pressure measurement mode, the intraocular pressure measurement device 20 is first retreated (to the negative side in the Z-axis direction) from a position where the intraocular pressure of one eye is measured, moved to the right-left direction (X-axis direction), and moved to a direction approaching the other inspected eye E, and thereby the alignment is executed. This operation is executed to prevent the tip of the air flow blowing nozzle 21b (the nozzle projection 21h described below) from coming in contact with the subject (nose and so on) erroneously.

In the embodiment, the controller 33 switches the position of the CCD camera to the first focusing position f1 and the second focusing position f2 in accordance with a position of the apparatus body 13 (the intraocular pressure measurement device 20) to the base 11, that is, a control position in the Z-axis direction (front-back direction) by the driver 12 (Z-axis driving part 12b). This is because the interval between the intraocular pressure measurement device 20 and the inspected eye E is roughly decided depending upon the position of the apparatus body 13 (the intraocular pressure measurement device 20) to the base 11. Note that the drive source of the focusing drive mechanism 21D is used together with the drive source of the fixation target moving mechanism 41D (see FIG. 4) of the fixation target projecting optical system 41 as described below. However, the drive source may share with a drive source of an index moving mechanism 43D (see FIG. 4) of a ring-shaped index projecting optical system for measuring eye-refractive power 43 (light-receiving optical system 44) as described below, or the foregoing mechanisms may have a drive source individually, without being limited to the embodiment.

In the anterior ocular segment observing optical system 21, an image of the anterior ocular segment of the inspected eye E is acquired by the CCD camera 21i while illuminating the inspected eye E (anterior ocular segment) by the anterior ocular segment illuminating light sources 21a. The image of the anterior ocular segment (light flux) passes outside the air flow blowing nozzle 21b, transmits the anterior ocular segment window glass 21c (including a glass plate 34b described below), the chamber window glass 21d, the half mirror 21g, and the half mirror 21e, is collected by the object lens 21f, and imaged on the CCD camera 21i (light-receiving surface). The CCD camera 21i (anterior ocular segment observing optical system 21) is configured to output a signal based on light reception of the image of the anterior ocular segment to the controller 33 (see FIG. 2). The controller 33 is configured to suitably display on the display 14 (see FIG. 1) the image of the anterior ocular segment acquitted by the CCD camera 21i (anterior ocular segment observing optical system 21).

Moreover, in the anterior ocular segment observing optical system 21, reflection light of X-Y alignment index light projected on the inspected eye E by the X-Y alignment index projecting optical system 22 on the cornea Ec is moved to the CCD camera 21i (the light-receiving surface), as described below. Specifically, in the anterior ocular segment observing optical system 21, the reflection light flux passes through an inside of the air flow blowing nozzle 21b, transmits the chamber window glass 21d, the half mirror 21g, and the half mirror 21e, and reaches the object lens 21f. Then, in the anterior ocular segment observing optical system 21, the reflection light is collected by the object lens 21f and moved to the CCD camera 21i. Then, an image of bright spot is imaged on the CCD camera 21i (light-receiving surface) at a position depending on a position relationship between the apparatus body 13 and the cornea Ec in the X-Y direction. The CCD camera 21i (the anterior ocular segment observing optical system 21) can output a signal based on light reception of the image of bright spot as imaged to the controller 33 (see FIG. 2). The image of bright spot of the X-Y alignment index light is formed on the cornea Ec of the inspected eye E. The controller 33 can therefore acquire an image (data) of the anterior ocular segment (cornea Ec) on which the image of bright spot is formed and can display on the display 14 the image of the anterior ocular segment (cornea Ec) formed with the image of bright spot. Note that an alignment auxiliary mark generated by an image generator which is not shown is together displayed on the display 14.

The X-Y alignment index projecting optical system 22 projects index light for X-Y alignment on the cornea Ec of the inspected eye E from the front. The index light has a function capable of executing the adjustment of a position of the inspected eye E to the intraocular pressure measurement device 20, that is, so-called alignment in the X-Y direction, as viewed in a direction along the X-Y plane (hereinafter also referred to as the X-Y direction). In addition, the index light also has a function that can detect a deformation amount (a degree of deformation (applanation)). The X-Y alignment index projecting optical system 22 includes a light source for X-Y alignment 22a, a condensing lens 22b, an aperture stop 22c, a pinhole plate 22d, a dichroic mirror 22e, and a projecting lens 22f, and shares the anterior ocular segment observing optical system 21 and the half mirror 21e. The light source for X-Y alignment 22a is configured to emit infrared light. The projecting lens 22f is disposed on a light path of the X-Y alignment index projecting optical system 22 to focus on the pinhole plate 22d. In the X-Y alignment index projecting optical system 22, the infrared light emitted from the light source for X-Y alignment 22a passes through the aperture stop 22c while being collected by the condensing lens 22b and is moved to the pinhole plate 22d (hole portion). In the X-Y alignment index projecting optical system 22, the light flux passing through the pinhole plate 22d (hole) is reflected on the dichroic mirror 22e and moved to the projecting lens 22f. The moved infrared light is formed as a parallel light flux by the projecting lens 22f and moved to the half mirror 21e. Then, in the X-Y alignment index projecting optical system 22, the parallel light flux is moved on the optical axis O1 of the anterior ocular segment observing optical system 21 by reflecting on the half mirror 21e. The parallel light flux transmits the half mirror 21g and the chamber window glass 21d and goes to the inside of the air flow blowing nozzle 21b, and reaches the inspected eye E as the X-Y alignment index light by passing through the inside of the air flow blowing nozzle 21b. The X-Y alignment index light is reflected on a surface of the cornea Ec so as to form the image of bright spot at an intermediate position between the apex Ea of the cornea Ec and a center of curvature of the cornea Ec, although it is not shown. Note that the aperture stop 22c is provided at a conjugate position with the apex Ea of the cornea Ec with respect to the projecting lens 22f.

The fixation target projecting optical system 23 projects (presents) the fixation target on the inspected eye E. The fixation target projecting optical system 23 includes a light source for fixation target 23a and a pinhole plate 23b and shares the X-Y alignment index projecting optical system 22, the dichroic mirror 22e, and the projecting lens 22f, as well as the anterior ocular segment observing optical system 21 and the half mirror 21e. The light source for fixation target 23a is configured to be a light source that emits visible light. In the fixation target projecting optical system 23, fixation target light emitted from the light source for fixation target 23a is moved to the pinhole plate 23b (a hole portion thereof) and passes through the pinhole plate 23*b* (hole portion), transmits the dichroic mirror 22*e*, and moved to the projecting lens 22*f*. The fixation target light (light flux) is formed in substantial parallel light by the projecting lens 22*f* and moved to the half mirror 21*e* and moves on the optical axis O1 of the anterior ocular segment observing optical system 21 by being reflected on the half mirror 21*e*. The light flux transmits the half mirror 21*g* and the chamber window glass 21*d*, moves to the inside of the air flow blowing nozzle 21*b*, passes through the inside of the air flow blowing nozzle 21*b*, and reaches the inspected eye E. The fixation target projecting optical system 23 fixes a line of sight of the subject by letting the subject gaze at the fixation target projected on the inspected eye E.

The applanation detecting optical system 24 receives the reflection light of the X-Y alignment index light projected on the inspected eye E by the X-Y alignment index projecting optical system 22 on the cornea Ec and detects the deformation amount (applanation) of the surface of the cornea Ec, as shown in FIG. 3. The applanation detecting optical system 24 includes a lens 24*a*, a pinhole plate 24*b*, a sensor 24*c*, and the half mirror 21*g* provided on the light path of the anterior ocular segment observing optical system 21. The lens 24*a* focuses on a central hole of the pinhole plate 24*b* the reflection light of the X-Y alignment index light on the cornea Ec, when the surface of the cornea Ec is flat. The pinhole plate 24*b* is provided to position the central hole at the light-focusing position as described above by the lens 24*a*. The sensor 24*c* is a light-receiving sensor that can detect a light quantity, and outputs a signal in accordance with a received light quantity. The sensor uses a photodiode in the embodiment. The sensor 24*c* (the applanation detecting optical system 24) outputs the signal in accordance with the received light quantity to the controller 33.

As described above, the reflection light flux of the X-Y alignment index light reflected on the surface (cornea surface) of the cornea Ec of the inspected eye E passes through the inside of the air flow blowing nozzle 21*b*, transmits the chamber window glass 21*d*, and reaches the half mirror 21*g*. In the applanation detecting optical system 24, a part of the reflection light flux is reflected on the half mirror 21*g* and moved to the lens 24*a*, condensed by the lens 24*a*, and moved to the pinhole plate 24*b*. Here, air flow is blown from the air flow blowing nozzle 21*b* to the cornea Ec of the inspected eye E by an air flow blowing mechanism 34 (see FIG. 1 and so on) as described below, thereby the surface of the cornea Ec gradually deforms to become a flat state. At this time, in the applanation detecting optical system 24, when the surface of the cornea Ec is flat by the foregoing setting, the entirety of the moved reflection light flux reaches the sensor 24*c* passing through the hole of the pinhole plate 24*b*. In the other state, the reflection light flux reaches the sensor 24*c* while being partially interrupted by the pinhole plate 24*b*. Therefore, by detecting a time at which the light quantity received on the sensor 24*c* is maximum, the flatness of the surface of the cornea Ec (applanation) can be detected. The applanation detecting optical system 24 can therefore detect a shape (applanation) of the surface of the cornea Ec deformed by blowing of the fluid and function as a light receiving part that receives the reflection light (reflection light flux) from the cornea Ec, which is detected by the sensor 24*c*.

The Z alignment index projecting optical system 25 projects alignment index light (alignment index parallel light flux) in the Z-axis direction on the cornea Ec of the inspected eye E from a diagonal direction, as shown in FIG. 2. The Z alignment index projecting optical system 25 is composed of a light source for Z alignment, a condensing lens 25*b*, an aperture stop 25*c*, a pinhole plate 25*d*, and a projecting lens 25*e* which are arranged on an optical axis O2. The light source for Z alignment 25*a* emits infrared light (for example, wavelength of 860 nm). The aperture stop 25*c* is disposed at a position conjugate with the apex Ea of the cornea Ec with respect to the projecting lens 25*e*. The projecting lens 25*e* is disposed to focus on the pinhole plate (hole portion). In the Z alignment index projecting optical system 25, the infrared light (light flux) emitted from the light source for Z alignment 25*b* passes through the aperture stop 25*c* while being condensed by the condensing lens 25*b* and goes to the pinhole plate 25*d*. In the Z alignment index projecting optical system 25, the light flux passing through the pinhole plate 25*d* (hole portion) is moved to the projecting lens 25*e* and is formed in parallel light in the projecting lens 25*e*, and the parallel light is moved to the cornea Ec. The infrared light (the flux light (Z alignment index light)) is reflected on the surface of the cornea Ec to form the image of bright spot positioning on the inside of the inspected eye E.

The Z alignment detecting optical system 26 receives the reflection light of the Z alignment index light on the cornea Ec from a symmetrical direction to the optical axis O1 of the anterior ocular segment observing optical system 21 and detects a positional relationship between the apparatus body 13 (intraocular pressure measurement device 20) and the cornea Ec in the Z-axis direction. The Z alignment detecting optical system 26 is composed of an imaging lens 26*a*, a cylindrical lens 26*b*, and a sensor 26*c* which are arranged on an optical axis O3. The cylindrical lens 26*b* has power in the Y-axis direction. The sensor 26*c* is a light-receiving sensor capable of detecting a light-receiving position on a light-receiving surface and can be configured by use of a line sensor or PSD (Position Sensitive Detector). In the embodiment, the line sensor is used. The sensor 26*c* is connected to a Z alignment detection corrector 32.

In the Z alignment detecting optical system 26, the alignment index light is projected on the cornea Ec by the Z alignment index projecting optical system 25, and the reflection flux reflected on the surface of the cornea Ec is moved to the imaging lens 26*a*. In the Z alignment detecting optical system 26, the reflection flux is focused by the imaging lens 26*a*, moved to the cylindrical lens 26*b*, and the image of bright spot is formed on the sensor 26*c* by being condensed in the Y-axis direction with the cylindrical lens 26*b*. The sensor 26*c* is in a conjugate positional relationship with respect to the image of bright spot formed inside the inspected eye E by the Z alignment index projecting optical system 25 and the imaging lens 26*a*, in the X-Z plane, and with respect to the apex Ea of cornea and the imaging lens 26*a*, and the cylindrical lens 26*b*, in the Y-Z plane. In other words, the sensor 26*c* is in a conjugate position with the aperture stop 25*c* (magnification at this time is set such that an image of the aperture stop 25*c* is lesser than a size of the sensor 26*c*), and even if the cornea Ec deviates in the Y-axis direction, the reflection flux on the surface of the cornea Ec is efficiently entered the sensor 26*c*. The sensor 26*c* (the Z alignment detecting optical system 26) outputs a signal based on light reception of the formed image of bright spot to the Z alignment detection corrector 32.

As shown in FIG. 3, the air flow blowing mechanism 34 includes an air compression chamber 34*a* in which an air compression drive device 34*d* (see FIG. 1) is provided. The air compression drive device 34*d* includes a movable piston in the air compression chamber 34*a* and an actuator that moves the piston. In the embodiment, the air compression drive device 34*d* is provided above the intraocular pressure measurement device 20 (optical system thereof) in the apparatus body 13. The air compression drive device 34d is driven under the control of the controller 33 (see FIG. 2) to compress air in the air compression chamber 34a. The air flow blowing nozzle 21b is attached to the air compression chamber 34a through the transparent glass plate 34b, and the chamber window glass 21d is disposed to face the air flow blowing nozzle. The air compression chamber 34a is therefore prevented from interrupting the above-described function in the anterior ocular segment observing optical system 21. Note that the air flow blowing nozzle 21b and the anterior ocular segment window glass 21c are contained in the nozzle projection 21h (see FIGS. 1, 6, and so on).

In addition, a pressure sensor 34c that detects a pressure of air in the air compression chamber 34a is provided in the air compression chamber 34a. The pressure sensor 34c is connected to the controller 33 (see FIG. 2), although it is not shown. The pressure sensor outputs a signal depending on the detected pressure to the controller 33. The air flow blowing mechanism 34 can blow the air flow from the air flow blowing nozzle 21b toward to the cornea Ec of the inspected eye E by compressing the air in the air compression chamber 34a by the air compression drive device 34d. By detecting the pressure in the air compression chamber 34a by the pressure sensor 34c, in the air flow blowing mechanism 34, it is possible to acquire a pressure when blowing the air flow from the air flow blowing nozzle 21b. Note that, in the air flow blowing mechanism 34, instead of providing the pressure sensor 34c, a change in pressure to a time may be set to be a predetermined characteristic in air flow to be blown.

The intraocular pressure measurement device 20 includes a driver (drive mechanism) that executes lighting control of the anterior ocular segment illuminating light source 21a, the light source for X-Y alignment 22a, the light source for fixation target 23a, and the light source for Z alignment 25a, and the controller 33 (see FIG. 2) is connected to the driver. As a result, in the intraocular pressure measurement device 20, the anterior ocular segment illuminating light source 21a, the light source for X-Y alignment 22a, the light source for fixation target 23a, and the light source for Z alignment 25a can be suitably lighted. In addition, in the intraocular pressure measurement device 20, as described above, under the control of the controller 33, the CCD camera 21i is suitably moved on the optical axis O1 through the focusing drive mechanism 21D, the generation processing of the image based on the image signal output from the CCD camera 21i is executed, and the generated image is suitably displayed on the display 14.

Next, schematic operation in measuring the intraocular pressure of the inspected eye E by use of the intraocular pressure measurement device 20 is described. Here, the following operation in the intraocular pressure measurement device 20 is executed under the control of the controller 33 (see FIG. 2). A power source switch of the ophthalmology apparatus 10 is first turned on and operation that executes measurement by use of the intraocular pressure measurement device 20 is displayed on the display 14. Hereupon, in the intraocular pressure measurement device 20, the anterior ocular segment illuminating light source 21a, the light source for X-Y alignment 22a, and the light source for fixation target 23a are suitably lighted after the intraocular pressure measurement mode (see FIG. 5A) is prepared, as described below. In this case, the flashing of each of the light sources 21a, 22a, and 23a can be repeated in a different cycle to distinguish whether it is light from which source, in the intraocular pressure measurement device 20.

In the intraocular pressure measurement device 20, the fixation target is projected on the inspected eye E by lighting the light source for fixation target 23a of the fixation target projecting optical system 23 to fix the inspected eye E, that is to say, to fix the visual line of the subject, as shown in FIG. 3. In addition, in the intraocular pressure measurement device 20, the parallel light flux is projected on the cornea Ec by lighting the light source for X-Y alignment 22a of the X-Y alignment index projecting optical system 22. In the intraocular pressure measurement device 20, the reflection light flux reflected on the cornea Ec is received on the CCD camera 21i of the anterior ocular segment observing optical system 21 and the sensor 24c of the applanation detecting optical system 24. Furthermore, in the intraocular pressure measurement device 20, the parallel light flux for alignment in the Z-axis direction is projected on the cornea Ec by lighting the light source for Z alignment 25a of the Z alignment index projecting optical system 25, as shown in FIG. 2. In the intraocular pressure measurement device 20, the reflection light flux reflected on the cornea Ec is received on the sensor 26c of the Z alignment detecting optical system 26.

In the intraocular pressure measurement device 20, the anterior ocular segment of the inspected eye E is illuminated by lighting the anterior ocular segment illuminating light source 21a of the anterior ocular segment observing optical system 21 and the image of the anterior ocular segment of the inspected eye E is imaged on the CCD camera 21i. In the intraocular pressure measurement device 20, the image of the anterior ocular segment of the inspected eye E, on which the image of bright spot of the X-Y alignment index light is formed, and the alignment auxiliary mark are displayed on the display 14, although they are clearly not shown. The examiner operates an operation part displayed on the display 14 while looking at the display 14, moves the apparatus body 13 upward, downward, rightward, and leftward, and executes the alignment such that the image of bright spot is displayed in a screen of the display 14. In addition, in the intraocular pressure measurement device 20, the Z alignment detection corrector 32 calculates a positional relationship between the apparatus body 13 and the cornea Ec in the Z-axis direction based on a light-receiving signal of the sensor 26c of the Z alignment detecting optical system 26 and a calculation result of an X-Y alignment detection part 31. In the intraocular pressure measurement device 20, the apparatus body 13 is suitably moved upward and downward (Y-axis direction), forward and backward (Z-axis direction), rightward and leftward (X-axis direction) relative to the base 11 to execute auto-alignment (automatic alignment adjustment) by suitably driving the driver 12, that is, the Y-axis driving part 12a, the Z-axis driving part 12b, and the X-axis driving part 12c based on the position in the X-Y direction acquired from the anterior ocular segment observing optical system 21 and the calculation result output from the Z alignment detection corrector 32, under the control of the controller 33.

In the intraocular pressure measurement device 20, when the auto-alignment is completed, the controller 33 operates the air flow blowing mechanism 34 to blow air flow from the air flow blowing nozzle 21b to the cornea Ec of the inspected eye E. Then, the surface of the cornea Ec is deformed to become a flat state (applanation) gradually. In a process where the cornea Ec becomes the flat state (applanation) gradually, when the surface of the cornea Ec is the flat state (applanation), the sensor 24c of the applanation detecting optical system 24 has the maximum light-receiving quantity. Therefore, in the intraocular pressure measurement device 20, the controller 33 determines that the surface of the cornea Ec is flattened (to be applanation) depending on a change in the light-receiving quantity of the sensor 24c. In other words, in the applanation detecting optical system 24 (sensor 24c), the applanation of the cornea Ec can be detected. Further, in the intraocular pressure measurement device 20, the controller 33 obtains the intraocular pressure (calculates a value of the intraocular pressure) of the inspected eye E based on the output (pressure of the blown air flow) from the pressure sensor 34c and displays the calculation result on the display 14. Here, the controller 33 may acquire the intraocular pressure (calculate a value of the intraocular pressure) of the inspected eye E based on a time from when the blowing of the air flow is initiated by the air flow blowing nozzle 21b (air flow blowing mechanism 34) to when the fact that the surface of the cornea Ec is flattened (applanation) is detected.

Next, an optical configuration of the eye characteristic measurement device 40 is described with reference to FIG. 4. The eye characteristic measurement device 40 measures a shape of the cornea Ec of the inspected eye E and refracting power (spherical power, astigmatic power, an angle of astigmatic axis, and so on) of the inspected eye E. The eye characteristic measurement device 40 includes the fixation target projecting optical system 41, an observation optical system 42, a ring-shaped index projecting optical system for measuring eye's refractive power 43, the light-receiving optical system 44, and an alignment light projecting system 45. The fixation target projecting optical system 41 projects the index on the eye ground Ef (see FIGS. 2 and 3) of the inspected eye E to let the inspected eye E make fixation and fogging. The observation optical system 42 observes the anterior ocular segment (cornea Ec) of the inspected eye E. The ring-shaped index projecting optical system for measuring eye's refractive power 43 projects a pattern light flux as a ring-shaped index for measuring eye's refractive power on the eye ground Ef of the inspected eye E to measure the eye's refractive power of the inspected eye E. The light-receiving optical system 44 receives an image of the ring-shaped index for measuring eye's refractive power, reflected on the eye ground Ef of the inspected eye E on an imager 44d as described below. The ring-shaped index projecting optical system for measuring eye's refractive power 43 and the light-receiving optical system 44 constitute an optical system for measuring the shape of the cornea and the eye's refractive power, together with the observation optical system 42 and ring-shaped index projecting light sources for measuring cornea shape 46A, 46B, and 46C as described below. The alignment light projecting system 45 projects index light to the inspected eye E to detect an alignment state in the X-Y direction. A working distance detecting optical system which is not shown is provided in an optical system of the eye characteristic measurement device 40 to detect a working distance between the inspected eye E and the apparatus body 13.

The fixation target projecting optical system 41 includes a fixation target light source 41a, a collimator lens 41b, an index plate 41c, a relay lens 41d, a mirror 41e, a dichroic mirror 41f, a dichroic mirror 41g, and an object lens 41h which are arranged on an optical axis O11. The index plate 41c is provided with a target to let the inspected eye E make fixation and fogging. The fixation target light source 41a, the collimator lens 41b, and the index plate 41c configure a fixation target unit 41U and are integrally movable along the optical axis O11 of the fixation target projecting optical system 41 by the fixation target moving mechanism 41D to let the inspected eye E make fixation and fogging. Here, positions where the dichroic mirror 41g and the object lens 41h are disposed are on a main optical axis O10 of the eye characteristic measurement device 40, as described below.

In the fixation target projecting optical system 41, visible light is emitted from the fixation target light source 41a, and after the visible light is formed in a parallel light flux by the collimator lens 41b, the parallel light flux is formed as a target light flux by passing through the index plate 41c. In addition, in the fixation target projecting optical system 41, the target light flux is reflected on the mirror 41e after it passes through relay lens 41d, passes through the dichroic mirror 41f, and goes to the dichroic mirror 41g. In the fixation target projecting optical system 41, the target light flux is reflected on the dichroic mirror 41g to go on the main optical axis O10 of the eye characteristic measurement device 40 and goes to the inspected eye E through the object lens 41h. The fixation target projecting optical system 41 fixes the visual line of the subject by letting the subject gaze at the target light flux (fixation target) projected on the inspected eye E as the fixation target. In addition, the fixation target projecting optical system 41 sets the inspected eye E to a fogging state by moving the fixation target unit 41U from a state letting the subject gaze at the fixation target to a position where the fixation target is not brought on focus.

The observation optical system 42 includes an illumination light source which is not shown and includes a half mirror 42a, a relay lens 42b, an imaging lens 42c, and an imager 42d, and shares the fixation target projecting optical system 41, the object lens 41h, and the dichroic mirror 41g. The imager 42d is a two-dimensional solid-state image sensor and uses a CMOS image sensor in the embodiment.

In the observation optical system 42, the anterior ocular segment (cornea Ec) of the inspected eye E is illuminated with an illumination light flux emitted from the illumination light source, and the illumination light flux reflected on the anterior ocular segment is acquired by the object lens 41h. In the observation optical system 42, the reflected illumination light flux passes through the object lens 41h, the dichroic mirror 41g, the half mirror 42a, the relay lens 42b, and is imaged on the imager 42d (light-receiving surface thereof) by the imaging lens 42c. The imager 42d outputs an image signal based on the acquired image to the controller 33 (see FIG. 2). The controller 33 displays the image of the anterior ocular segment (cornea Ec) on the display 14 based on the input image signal. In the observation optical system 42, it is therefore possible to form the image of the anterior ocular segment (cornea Ec) on the imager 42d (the light-receiving surface) and display the image of the anterior ocular segment on the display 14. Here, when measuring the refractive power after the alignment completion, the illumination light source of the observation optical system 42 is turned off.

The ring-shaped index projecting optical system for measuring eye's refractive power 43 includes a light source for measuring eye's refractive power 43a, a lens 43b, a conical prism 43c, a ring index plate 43d, a lens 43e, a band pass filter 43f, a pupil ring 43g, a perforated prism 43h, and a rotary prism 43i and shares the fixation target projecting optical system 41, the dichroic mirror 41f, the dichroic mirror 41g, and the object lens 41h. The light source for measuring eye's refractive power 43a and the pupil ring 43g are arranged in an optically conjugate position, and the ring index plate 43d and the eye ground Ef of the inspected eye E are arranged in an optically conjugate position. In addition, the light source for measuring eye's refractive power 43a, the lens 43b, the conical prism 43c, and the ring index plate 43d constitute an index unit 43U. The index unit 43U is integrally movable along an optical axis O13 of the ring-shaped index projecting optical system for measuring eye's refractive power 43 by the index moving mechanism 43D.

In the ring-shaped index projecting optical system for measuring eye's refractive power 43, the light flux emitted from the light source for measuring eye's refractive power 43a forms in a parallel light flux by the lens 43b and the parallel light flux goes to the ring index plate 43d through the conical prism 43c. The parallel light flux transmits a ring-shaped pattern portion provided on the ring index plate 43d to be formed in a pattern light flux as a ring-shaped index for measuring eyes refractive power. In the ring-shaped index projecting optical system for measuring eye's refractive power 43, the pattern light flux is moved to the perforated prism 43h through the lens 43e, the band pass filter 43f, and the pupil ring 43g, reflected on a reflection surface of the perforated prism 43h, and moved to the dichroic mirror 41f through the rotary prism 43i. Then, in the ring-shaped index projecting optical system for measuring eye's refractive power 43, the pattern light flux is reflected on the dichroic mirror 41g after it is reflected on the dichroic mirror 41f, thereby moving to the main optical axis O10 of the eye characteristic measurement device 40. Furthermore, in the ring-shaped index projecting optical system for measuring eye's refractive power 43, the pattern light flux is imaged on the eye ground Ef (see FIGS. 2 and 3) of the inspected eye E by the object lens 41h.

The ring-shaped index projecting optical system for measuring eye's refractive power 43 is provided with ring-shaped index projecting light sources for measuring cornea shape 46A, 46B, and 46C disposed in front of the object lens 41h. The ring-shaped index projecting light sources for measuring cornea shape 46A, 46B, and 46C are arranged at a predetermined distance from the inspected eye E (cornea Ec) on the ring pattern 47 and coaxially arranged with respect to the optical axis O10, and project ring-shaped index light for measuring cornea shape on the inspected light E (cornea Ec). A ring-shaped index for measuring cornea shape is formed on the cornea Ec by projecting the ring-shaped index light for measuring cornea shape on the cornea Ec of the inspected light E. The ring-shaped index (light flux thereof) for measuring cornea shape is reflected on the cornea Ec of the inspected light E, and thereby the ring-shaped index is imaged on the imager 42d by the observation optical system 42. In the observation optical system 42, it is therefore possible to display an image of the ring-shaped index for measuring cornea shape on the display 14 to overlap on the image of the anterior ocular segment (cornea Ec).

The light-receiving optical system 44 includes a hole 44a of the perforated prism 43h, a mirror 44b, a lens 44c, and an imager 44d, and shares the fixation target projecting optical system 41, the object lens 41h, the dichroic mirror 41g, the dichroic mirror 41f, and the ring-shaped index projecting optical system for measuring eye's refractive power 43 and the rotary prism 43i. The imager 44d is a two-dimensional solid-state image sensor and uses a CCD (Charge Coupled Device) image sensor in the embodiment. The imager 44d is movable along an optical axis O14 of the light-receiving optical system 44 by the index moving mechanism 43D in conjunction with the index unit 43U of the ring-shaped index projecting optical system for measuring eye's refractive power 43.

In the light-receiving optical system 44, the pattern reflection light flux guided to the eye ground Ef (see FIGS. 2 and 3) by the ring-shaped index projecting optical system for measuring eye's refractive power 43 and reflected on the eye ground Ef is focused by the object lens 41h and reflected on the dichroic mirror 41f after it is reflected on the dichroic mirror 41g, and moved to the rotary prism 43i. Then, in the light-receiving optical system 44, the reflected pattern reflection light flux is moved to the hole 44a of the perforated prism 43h through the rotary prism 43i and passes through the hole 44a. In the light-receiving optical system 44, the pattern reflection light flux passed through the hole 44a is reflected on the mirror 44b and is configured to image the pattern reflection light flux, that is, the ring-shaped index for measuring eye's refractive power on the imager 44d (the light-receiving surface) by the lens 44c. The imager 44d outputs an image signal based on the acquired image to the controller 33 (see FIG. 2). The controller 33 displays the image of the ring-shaped index for measuring eye's refractive power on the display 14 (see FIG. 1) based on the input image signal. In the light-receiving optical system 44, it is therefore possible to form the image of the ring-shaped index for measuring eye's refractive power on the imager 44d (light-receiving surface) and display the image of the ring-shaped index for measuring eye's refractive power on the display 14.

The alignment light projecting system 45 includes an LED 45a, a pinhole 45b, and a lens 45c and shares the observation optical system 42 and the half mirror 42a, and the fixation target projecting optical system 41, the dichroic mirror 41g and the object lens 41h. In the alignment light projecting system 45, the light flux emitted from the LED 45a passes through the pinhole 45b (hole thereof) to be an alignment index light flux, is reflected on the half mirror 42a through the lens 45c, and moved onto the main optical axis O10 of the eye characteristic measurement device 40. Then, in the alignment light projecting system 45, the alignment index light flux passes through the dichroic mirror 41g and is moved to the object lens 41h, and projected on the cornea Ec of the inspected eye E as the alignment index light flux passing through the object lens 41h. The alignment light projecting system 45 has a function to automatically align the apparatus body to the inspected eye E by projecting the alignment index light flux on the cornea Ec of the inspected eye E. The alignment index light flux projected on the inspected eye E as the parallel light is reflected on the cornea Ec of the inspected eye E, and the image of bright spot as an alignment index image is projected on the imager 42d by the observation optical system 42. When the image of bright spot is positioned in an alignment mark formed by an optical system which is not shown, the alignment is completed.

The eye characteristic measurement device 40 includes a driver (drive mechanism) that executes lighting control of the fixation target light source 41a, the illumination light source of the observation optical system 42, the light source for measuring eye's refractive power 43a, the LED 45a, and the light sources for measuring cornea shape 46A, 46B, 46C. The controller 33 (see FIG. 2) is connected to the driver. In the eye characteristic measurement device 40, the fixation target light source 41a, the illumination light source of the observation optical system 42, the light source for measuring eye's refractive power 43a, the LED 45a, and the light sources for measuring cornea shape 46A, 46B, 46C are therefore suitably lighted under the control of the controller 33. Moreover, in the eye characteristic measurement device 40, under the control of the controller 33, the fixation target unit 41U is integrally moved by the fixation target moving mechanism 41D along the optical axis O13, and the index unit 43U is integrally moved by the index moving mechanism 43D along the optical axis O13 and the imager 44d is moved along the optical axis O14, as described above. Furthermore, in the eye characteristic measurement device 40, under the control of the controller 33, generation processing of images is executed based on image signals output from the imagers 42d and 44d and the generated images are suitably displayed on the display 14, as described above.

Next, schematic operation in measuring the shape of the cornea Ec of the inspected eye E and the refractive power (the spherical power, the astigmatic power, the astigmatic axis angle, and so on) of the inspected eye E by use of the eye characteristic measurement device 40 is described. Note that the following operation in the eye characteristic measurement device 40 is executed under the control of the controller 33 (see FIG. 2). The power source of the ophthalmology apparatus 10 is first turned on to display operation that executes measurement by use of the eye characteristic measurement device 40 on the display 14. As a result, after the eye characteristic measurement mode (see FIG. 5B) is formed in the eye characteristic measurement device 40, the image of the anterior ocular segment (cornea Ec) is displayed on the display 14 by lighting the illumination light source in the observation optical system 42. Then, the examiner operates the operation part displayed on the display 14 such that the pupil of the inspected eye E is positioned in the screen of the display 14 to move the apparatus body 13 upward and downward, and rightward and leftward, thereby executing the schematic alignment of the apparatus body 13 relative to the inspected eye E. Here, in the eye characteristic measurement device 40 (controller 33), it is possible to detect the pupil from the image of the anterior ocular segment based on the image signal output from the imager 42d. The detection of the pupil is executed, for example, by previously storing a shape to be recognized as the pupil in the image of the anterior ocular segment and detecting the shape to be recognized based on contrast in the image. Therefore, in the eye characteristic measurement device 40, for example, in a case where the inspected eye E which is the target of the measurement is switched rightward and leftward, the above-described schematic alignment can be automatically executed by detecting the pupil based on the image while rightward and leftward moving the apparatus body 13 in accordance with the switching and moving the apparatus body 13 (the eye characteristic measurement device 40) considering the detected pupil to be the target position.

As a result, in the eye characteristic measurement device 40, the image of bright spot as the alignment index image is displayed on the display 14 by the observation optical system 42. Thereafter, in the eye characteristic measurement device 40, the alignment detection based on the alignment light projecting system 45 and the working distance detecting optical system (not shown) is initiated. That is to say, in the eye characteristic measurement device 40, the automatic alignment (adjustment of automatic alignment) is executed by suitably moving the apparatus body 13 upward and downward (Y-axis direction), forward and backward (Z-axis direction), and rightward and leftward (X-axis direction) relative to the base 11 to position the image of bright spot as the alignment index image in the alignment mark. Thereby, in the eye characteristic measurement device 40, the automatic alignment of the apparatus body 13 relative to the apex of the cornea Ec of the inspected eye E is completed.

Consequently, in the eye characteristic measurement device 40, the light sources for measuring cornea shape 46A, 46B, 46C of the ring-shaped index projecting optical system for measuring eye's refractive power 43 are lighted to project the ring-shaped index for measuring cornea shape on the cornea Ec. Then, in the controller 33, the shape of the cornea Ec is measured from the image of the ring-shaped index for measuring cornea shape projected on the cornea Ec based on the image (image signal from the imager 42d) displayed on the display 14. A description of measurement of shape of the cornea Ec is omitted since a detail thereof is known. The controller 33 can measure the spherical power, the astigmatic power, and the astigmatic axis angle as the eye's refractive power by a well-known measurer. Note that a configuration of the well-known measurer for the eye's refractive power is the same as that disclosed in JP2002-253506A, but is not limited to this. In this way, the controller 33 executes the measurement of the shape of the cornea Ec and the measurement of the eye's refractive power (optical characteristic). Note that the controller 33 suitably stores an operation result and so on in a storage (not shown).

In the ophthalmology apparatus 10 in the embodiment, the intraocular pressure measurement device 20 is provided above the eye characteristic measurement device 40, and the intraocular pressure measurement device 20 and the eye characteristic measurement device 40 are attached to an attachment base and fixed to each other. In other words, in the ophthalmology apparatus 10, the intraocular pressure measurement device 20 and the eye characteristic measurement device 40 are integrally configured so that it is not necessary to change a positional relationship therebetween. The attachment base, that is, the intraocular pressure measurement device 20 and the eye characteristic measurement device 40 attached to the attachment base (apparatus body 13) are suitably moved upward and downward (Y-axis direction), forward and backward (Z-axis direction), and rightward and leftward (X-axis direction) relative to the base 11 by the driver 12, that is, the Y-axis driving part 12a, the Z-axis driving part 12b, and the X-axis driving part 12c. Then, in the ophthalmology apparatus 10, by moving the apparatus body 13 relative to the base 11 by the driver 12 (the Y-axis driving part 12a, the Z-axis driving part 12b, and the X-axis driving part 12c), each of the intraocular pressure measurement device 20 and the eye characteristic measurement device 40 can be moved to a position corresponding to the inspected eye E (face of the subject) fixed by the jaw rest 15 and the forehead support 16 (see FIGS. 5A and 5B).

In the ophthalmology apparatus 10, by moving the apparatus body 13 (attachment base) upward and downward (Y-axis direction) relative to the base 11 by the Y-axis driving part 12a of the driver 12, the intraocular pressure measurement device 20 can be adapted to correspond to a height position of the inspected eye E by positioning the inspected eye E on an extension line of the optical axis O1 of the anterior ocular segment observing optical system 21 of the intraocular pressure measurement device 20 (see FIG. 5A). In the ophthalmology apparatus 10, the tip of the air flow blowing nozzle 21b (nozzle projection 21h) of the anterior ocular segment observing optical system 21 of the intraocular pressure measurement device 20 is positioned from the inspected eye E (apex Ea of the cornea) to the second setting working distance d2 by forward and backward (in Z-axis direction) moving the apparatus body by the Z-axis driving part 12b of the driver 12, as shown in FIG. 5A. The second setting working distance d2 is 11 mm in the embodiment. This state is the measurement mode, that is, the intraocular pressure measurement mode.

Also, in the ophthalmology apparatus 10, by upward and downward (in Y-axis direction) moving the apparatus body 13 (attachment base) relative to the base 11 by the Y-axis driving part 12a of the driver 12, the inspected eye E is positioned on an extension line of the main optical axis O10 of the eye characteristic measurement device 40 to be capable of corresponding the eye characteristic measurement device 40 to a height position of the inspected eye E (see FIG. 5B). In the ophthalmology apparatus 10, a front end (a ring pattern 47 in the embodiment) of the eye characteristic measurement device 40 is positioned from the inspected eye E to the first setting working distance d1 by forward and backward (in Z-axis direction) moving the apparatus body by the Z-axis driving part 12b of the driver 12, as shown in FIG. 5B. Note that the front end of the eye characteristic measurement device 40 means a part closest to the subject in the eye characteristic measurement device 40, the part is the ring pattern 47 in the embodiment. The first setting working distance d1 is about 80 mm in the embodiment. This state is the measurement mode by the eye characteristic measurement device 40, that is, the eye characteristic measurement mode.

In the ophthalmology apparatus 10, following the above, a front end (air flow blowing nozzle 21b (nozzle projection 21h)) of the intraocular pressure measurement device 20 is displaced from the front end (ring pattern 47) of the eye characteristic measurement device 40 to the positive side (subject's side) in the Z-axis direction, in the embodiment. This is for the following reason. When the ophthalmology apparatus 10 is in the intraocular pressure measurement mode in accordance with the above configuration, the ring pattern 47 which is the front end of the eye characteristic measurement device 40 is positioned in front of the nose or the mouth of the subject, as shown in FIG. 5A. In addition, in the ophthalmology apparatus 10, the intraocular pressure measurement device 20 and the eye characteristic measurement device 40 are integrally configured not to change the positional relationship. If the front end of the intraocular pressure measurement device 20 and the front end of the eye characteristic measurement device 40 are therefore in an equal position as viewed in the Z-axis direction (forward and backward), for example, in the ophthalmology apparatus 10, the ring pattern 47 is in contact with the nose or the mouth of the subject, or the ring pattern 47 gives a sense that it is an obstacle to the subject, even though the ring pattern 47 is not in contact with the nose or the mouth of the subject, in the intraocular pressure measurement mode. In view of this, in the ophthalmology apparatus 10, a space is secured in front of the nose or the mouth of the subject at the time of the intraocular pressure measurement mode by displaying the front end (air flow blowing nozzle 21b (nozzle projection 21h)) of the intraocular pressure measurement device 20 to the positive side in the Z-axis direction from the front end (ring pattern 47) of the eye characteristic measurement device 40.

In the ophthalmology apparatus 10, following the above, the first setting working distance d1 from the inspected eye E (apex Ea of the cornea) when executing the measurement to the front end (ring pattern 47 in the embodiment) of the eye characteristic measurement device 40 in the embodiment is 75 mm or more (80 mm in the embodiment). This is for the following reason. The first setting working distance d1 is a distance capable of executing the measurement of the inspected eye E by the eye characteristic measurement device 40. This distance becomes a reference position in a case where the eye characteristic measurement device is moved in the Z-axis direction in accordance with the inspected eye E (the state thereof) when executing the measurement by the eye characteristic measurement device 40. Therefore, in the eye characteristic measurement device 40, a moving width to move from the first setting working distance d1 to the positive side and the negative side in the Z-axis direction is set. The moving width is ±20 mm in the embodiment. Moreover, in the ophthalmology apparatus 10, the front end (air flow blowing nozzle 21b (nozzle projection 21h)) of the intraocular pressure measurement device 20 is displayed from the front end (ring pattern 47) of the eye characteristic measurement device 40 to the positive side in the Z-axis direction, as described above. Thereby, in the ophthalmology apparatus 10, in the case of the eye characteristic measurement mode, the air flow blowing nozzle 21b (nozzle projection 21h) which is the front end of the intraocular pressure measurement device 20 is positioned to face the forehead support 16 fixing the face of the subject together with the jaw rest 15, as shown in FIG. 5B. Accordingly, in the ophthalmology apparatus 10, there is a possibility that the front end (the air flow blowing nozzle 21b (nozzle projection 21h)) of the intraocular pressure measurement device 20 interferes with the forehead support 16 when moving to the positive side (subject side) in the Z-axis direction with the moving width as described above, if the first setting working distance d1 in the eye characteristic measurement device 40 is small. In other words, in the ophthalmology apparatus 10, it is necessary to increase the first setting working distance d1 to allow the eye characteristic measurement device 40 to move from the first setting working distance d1 in the Z-axis direction with the moving width as described above. From this, in the ophthalmology apparatus 10, the first setting working distance d1 is set to be 75 mm or more in the eye characteristic measurement device 40 and is about 80 mm in the embodiment. Note that the setting of the first setting working distance d1 can execute by adjusting the setting of each optical member in the eye characteristic measurement device 40. Therefore, in the ophthalmology apparatus 10, even if the front end (air flow blowing nozzle 21b (nozzle projection 21h)) of the intraocular pressure measurement device 20 is displayed from the front end (ring pattern 47) of the eye characteristic measurement device 40 to the positive side in Z-axis direction, the front end (air flow blowing nozzle 21b (nozzle projection 21h)) of the intraocular pressure measurement device 20 is certainly prevented from interfering with the forehead support 16 in the eye characteristic measurement mode.

In the ophthalmology apparatus 10, in general, after the shape of the cornea Ec of the inspected eye E and the refractive power (the spherical power, the astigmatic power, the astigmatic axis angle, and so on) of the inspected eye E are measured by the eye characteristic measurement device 40, the intraocular pressure of the inspected eye E is measured by the intraocular pressure measurement device 20. In the ophthalmology apparatus 10, the controller 33 (see FIG. 2) controls the operation of each part based on the operations displayed on the display 14, as described above.

In the ophthalmology apparatus 10, when the power switch is turned on, an intraocular pressure witching icon which is the intraocular pressure measurement mode and an eye characteristic switching icon which is the eye characteristic measurement mode are displayed on the display 14. Here, in the display 14, if selection and switching of the intraocular pressure measurement mode and the eye characteristic measurement mode can be executed, instead of the display of the intraocular pressure witching icon and the eye characteristic measurement mode, a single switching icon or other type icon may be displayed, without being limited to the configuration in the embodiment. In addition, an order of the measurement is previously set, after the measurement of the right and left eyes by the eye characteristic measurement device 40, this measurement may be automatically transferred to the measurement (intraocular pressure measurement mode) by the intraocular pressure measurement device 20. In the embodiment, the eye characteristic switching icon of the display has been touched (selected) to previously measure the shape of the cornea Ec of the inspected eye E and the refractive power (the spherical power, the astigmatic power, the astigmatic axis angle, and so on) of the inspected eye E by the eye characteristic measurement device 40.

Accordingly, in the ophthalmology apparatus 10, the eye characteristic measurement mode is set by suitably driving the Y-axis driving part 12a, the Z-axis driving part 12b, and the X-axis driving part 12c of the driver 12 (see FIG. 5B). In other words, in the ophthalmology apparatus 10, the eye characteristic measurement device 40 is configured to correspond to the inspected eye E so as to position the inspected eye E on the extension line of the main optical axis O10 of the eye characteristic measurement device 40 and the object lens 41h of the fixation target projecting optical system 41 of the eye characteristic measurement device 40 from the inspected eye E to the first setting working distance d1, as shown in FIG. 5B. As a result, in the ophthalmology apparatus 10, the shape of the cornea Ec of the inspected eye E and the refractive power (the spherical power, the astigmatic power, the astigmatic axis angle, and so on) of the inspected eye E are measured by the above-mentioned operation of the eye characteristic measurement device 40. Thereafter, the eye characteristic switching icon of the display has been touched (selected) to measure the intraocular pressure of the inspected eye E.

Accordingly, in the ophthalmology apparatus 10, the intraocular pressure measurement mode is set by suitably driving the Y-axis driving part 12a, the Z-axis driving part 12b, and the X-axis driving part 12c of the driver 12 (see FIG. 5A). Here, in the ophthalmology apparatus 10, the apparatus body 13 is first moved to the negative side in the Y-axis direction to set the intraocular pressure measurement device 20 to a height position corresponding to the inspected eye E. At this time, in the ophthalmology apparatus 10, the position on the optical axis O1 of the CCD camera 21i by the focusing drive mechanism 21D is set to be the second focus position f2 (see FIG. 3). Thereby, in the ophthalmology apparatus 10, the image of the inspected eye E (the anterior ocular segment (cornea Ec)) can be suitably displayed on the display 14. Thereafter, in the ophthalmology apparatus 10, the apparatus body 13 is moved to the positive side in the Z-axis direction to approximate the intraocular pressure measurement device 20 to the inspected eye E and the intraocular pressure measurement device 20 corresponds to the inspected eye E to position the tip of the air flow blowing nozzle 21b (nozzle projection 21h) from the inspected eye E to the second setting working distance d2, as shown in FIG. 5A. At this time, in the ophthalmology apparatus 10, the position on the optical axis O1 of the CCD camera 21i is moved to the first focus position f1 (see FIG. 3) by the focusing drive mechanism 21D. Thereby, in the ophthalmology apparatus 10, the image of the inspected eye E (the anterior ocular segment (cornea Ec)) can be suitably displayed on the display 14. In addition, in the ophthalmology apparatus 10, the intraocular pressure of the inspected eye E is measured by the above-mentioned operation of the intraocular pressure measurement device 20.

Thereby, in the ophthalmology apparatus 10, the shape of the cornea Ec of the inspected eye E and the refractive power (the spherical power, the astigmatic power, the astigmatic axis angle, and so on) of the inspected eye E can be measured by the eye characteristic measurement device 40 and the intraocular pressure of the inspected eye E can be measured by the intraocular pressure measurement device 20.

Next, a characteristic configuration of the ophthalmology apparatus 10 according to the present invention is described with reference to FIGS. 6 to 10A and 10B. Here, in FIG. 6, a positional relationship between the nozzle projection 21h (apparatus body 13) and the forehead support 16 at the height position HL is shown, but this merely shows a concept of the height position intelligibly and does not necessarily correspond to a positional relationship in an actual apparatus. In FIGS. 7A to 7D, a positional relationship between the nozzle projection 21h (apparatus body 13) and the forehead support 16 at each front position is shown, but this merely shows a concept of each front position intelligibly and does not necessarily correspond to a positional relationship in an actual apparatus.

Figure 6:
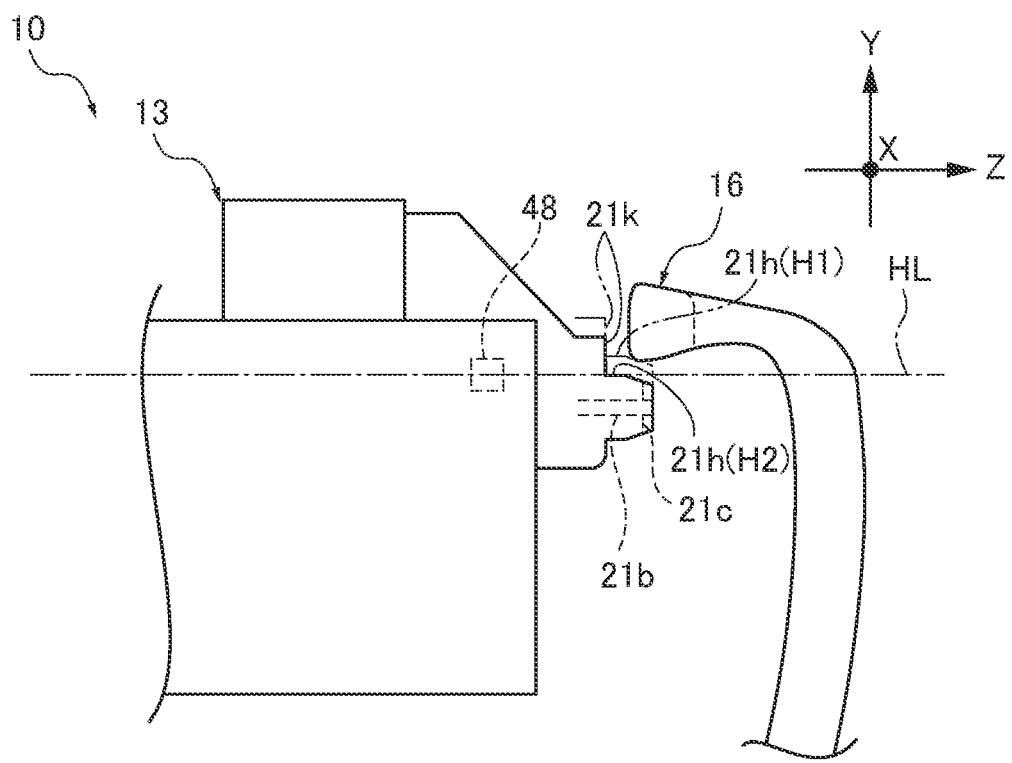
FIG. 6 is an explanatory view for explaining a height position HL by use of a positional relationship between a nozzle projection 21h (the apparatus body 13) and a forehead support 16.

In the ophthalmology apparatus 10, a height position detector 48 that detects that the apparatus body 13 reaches the predetermined height position HL is provided on the apparatus body 13, as shown in FIG. 6. The height position HL is set from a viewpoint preventing the nozzle projection 21h (air flow blowing nozzle 21b) of the intraocular pressure measurement device 20 from interfering with the forehead support 16. When the apparatus body 13 reaches the height position HL, the height position detector 48 outputs a signal representing the fact to the controller 33 (see FIG. 2). Therefore, when the controller 33 receives the signal that the apparatus body 13 reaches the height position HL from the height position detector 48, the nozzle projection 21h (air flow blowing nozzle 21b) of the intraocular pressure measurement device 20 is positioned at a first height position H1 (see the nozzle projection 21h shown in an imaginary line, and FIGS. 7A and 7B capable of interfering with the forehead support 16. On the contrary, when the controller 33 does not receive the signal from the height position detector 48, the nozzle projection 21h (air flow blowing nozzle 21b) of the intraocular pressure measurement device 20 is positioned at a second height position H2 (see the nozzle projection 21h shown in an imaginary line, and FIGS. 7C and 7D which does not interfere with the forehead support 16. When the controller 33 acquires the signal from the height position detector 48, it stops the upward moving of the apparatus body 13 in the case of the intraocular pressure measurement mode, or in a case where the intraocular pressure measurement device 20 exists in the positive side (subject side) of the Z-axis direction from a predetermined forward and backward position. The predetermined forward and backward position is set from a viewpoint preventing the air flow blowing nozzle 21b from interfering with the forehead support 16 as viewed in the Z-axis direction and uses the first front position FL1 (see FIG. 7A) as described below in the embodiment.

When the controller 33 acquires the signal that the apparatus body 13 reaches the height position HL from the height position detector 48, the controller stops the upward movement of the apparatus body 13 and executes control depending on a situation of moving the apparatus body 13 upward (positive side in the Y-axis direction). As the control depending on the situation, for example, it is pointed out to display on the display 14 that the apparatus body cannot be further moved in a case where the apparatus body 13 is moved upward based on the operation executed on the display 14, or the apparatus body 13 is moved upward after the apparatus body 13 is retreated (moved) backward (negative side in the Z-axis direction) in the forward and backward direction. In addition, as the control depending on the situation, for example, it is pointed out that the apparatus body 13 is moved upward after the apparatus body 13 is retreated (moved) backward (negative side in the Z-axis direction) in the forward and backward direction, in the case of moving the apparatus body to switch from the intraocular pressure measurement device 20 to the eye characteristic measurement device 40. Furthermore, in the controller 33, when executing the automatic alignment in the intraocular pressure measurement device 20, when acquiring the signal from the height position detector 48, the inspected eye E is detected again. This is because letting the apparatus body 13 reach the height position HL when executing the automatic alignment in the intraocular pressure measurement device 20 means to fail in detecting the inspected eye E which is a standard of the alignment.

When the power switch of the ophthalmology apparatus 10 is turned on, the controller 33 determines whether the signal that the apparatus body 13 reaches the height position HL is output from the height position detector 48 before executing the movement of the apparatus body 13. If the signal is not output from the height position detector 48, the controller 33 executes the movement of the apparatus body 13. If the signal is output from the height position detector 48, the controller 33 does not execute the upward movement of the apparatus body 13 and executes control depending on a situation. As the control depending on the situation, for example, it is pointed out to display on the display 14 that the apparatus body 13 cannot be further upward moved, if the operation moving upward the apparatus body 13 is executed in the display 14, or move upward the apparatus body 13 after the apparatus body 13 is retreated (moved) backward (negative side in the Z-axis direction) in the forward and backward direction. As the control depending on the situation, for example, it is pointed out to move upward the apparatus body 13 after the apparatus body 13 is retreated (moved) backward (negative side in the Z-axis direction) in the forward and backward direction, in the case of moving the apparatus body to switch from the intraocular pressure measurement device 20 to the eye characteristic measurement device 40. As a result, in the ophthalmology apparatus 10, for example, even if the operation of switching from the intraocular pressure measurement device 20 to the eye characteristic measurement device 40 is executed and the power switch is turned off in a state where the height position detector 48 outputs the above-mentioned signal, it is possible to move the apparatus body 13 while certainly preventing the nozzle projection 21*h* (air flow blowing nozzle 21*b*) from interfering with the forehead support 16, when the power switch is turned on again. Here, although the height position detector 48 is provided on the apparatus body 13 in an example shown in FIG. 6, it actually may be provided on the Y-axis driving part 12*a* of the driver 12, controlling the height direction, that is, the position in the Y-axis direction of the apparatus body 13, or on places without being limited to the embodiment.

In the ophthalmology apparatus 10, a front position detector 49 that detects that the apparatus body 13 reaches each of the front positions (FL1 to FL4) is provided on the apparatus body 13, as shown in FIGS. 7A to 7D. As the front positions, the first front position FL1, the second front position FL2, the third front position FL3, and the fourth front position FL4 are set in the embodiment. The front positions (FL1 to FL4) represent the tip of the nozzle projection 21*h* (air flow blowing nozzle 21*b*) as the standard, in an example shown in FIGS. 7A to 7D. This is because the understanding can be easily accomplished by representing the tip as the standard from that the first front position FL1 and the second front position FL2 are set to be provided at a predetermined interval between the tip of the nozzle projection 21*h* (air flow blowing nozzle 21*b*) and the forehead support 16. Even regarding the third front position FL3 and the fourth front position FL4, the understanding can be easily accomplished by using the same standard as in the first front position FL1 and the second front position FL2.

The first front position FL1 is set from a viewpoint of preventing the nozzle projection 21*h* (air flow blowing nozzle 21*b*) of the intraocular pressure measurement device 20 from interfering with the forehead support 16 in the case of the eye characteristic measurement mode, basically, as shown in FIG. 7A. In other words, the first front position FL1 is set to be capable of providing a first interval i1 between the tip of the nozzle projection 21*h* and the forehead support 16 when the apparatus body 13 is disposed at the first height position H1 at which the nozzle projection 21*h* (air flow blowing nozzle 21*b*) and the forehead support 16 can be interfered. The first interval i1 is set to be a small value as possible on the assumption that the tip of the nozzle projection 21*h* (air flow blowing nozzle 21*b*) can be certainly prevented from interfering with the forehead support 16. The first interval i1 is set to be 1 mm in the embodiment. The first front position FL1 is therefore set to be 1 mm as the position of the apparatus body 13, which is the first interval i1 between the tip of the nozzle projection 21*h* and the forehead support 16, in the embodiment. The first interval i1 (first front position FL1) may be suitably set, without being limited to the embodiment. In addition, the first interval i1 may be suitably set by a user (examiner).

Figure 8:
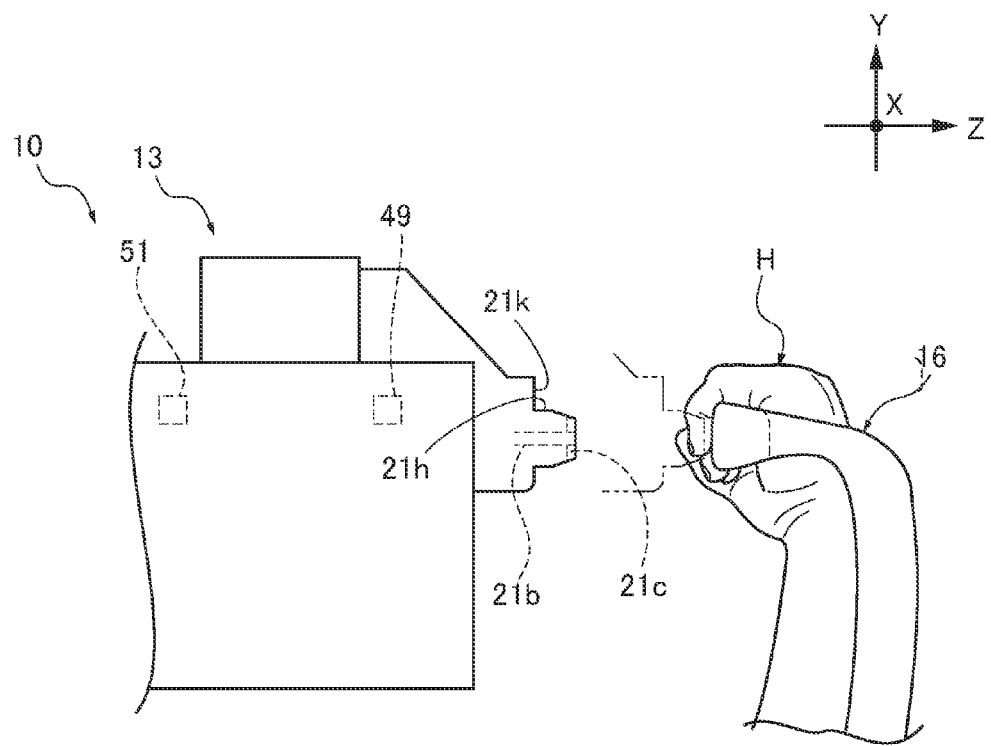
FIG. 8 is an explanatory view showing a state where a hand H is put on the forehead support 16.

The second front position FL2 is set to be capable of providing a second interval i2 larger than the first interval i1 between the tip of the nozzle projection 21*h* and the forehead support 16, in the case of the eye characteristic measurement mode, basically, as shown in FIG. 7B. The second interval i2 is set from a viewpoint preventing the hand H (see FIG. 8) put on the forehead support 16 from being interposed between the nozzle projection 21*h* (air flow blowing nozzle 21*b*) of the intraocular pressure measurement device 20 and the forehead support 16 when the apparatus body 13 is disposed at the first height position H1 at which the nozzle projection 21*h* (air flow blowing nozzle 21*b*) and the forehead support 16 can be interfered. This is because it is considered that the subject grips the forehead support 16 with the hand H (engaging the hand with the forehead support) to stabilize the subject's face, as shown in FIG. 8. In addition, this is because it is considered that, for example, the examiner is in contact with the forehead support when the examiner opens the eyelid of the subject, although it is not shown. In this way, the second interval i2 is set from the viewpoint that the hand H is prevented from being interposed between the nozzle projection 21*h* (air flow blowing nozzle 21*b*) and the forehead support 16 and is 15 mm in the embodiment. The second front position FL2 is therefore set to be 15 mm as the position of the apparatus body 13, which is the second interval i2 between the tip of the nozzle projection 21*h* and the forehead support 16, in the embodiment. The second interval i2 (second front position FL2) may be suitably set, without being limited to the embodiment. In addition, the first interval i1 may be suitably set by the user (examiner).

The third front position FL3 is set from a viewpoint preventing the hand H (see FIG. 8) put on the forehead support 16 from being interposed between a wall portion 21*k* of the air flow blowing mechanism, which is an outer wall surface above the nozzle projection 21*h* and the forehead support 16 in the intraocular pressure measurement device 20 (apparatus body 13), in the case of the eye characteristic measurement mode, basically, as shown in FIG. 7C. The third front position FL3 is therefore set to be capable of providing the second interval i2 between the wall portion 21k of the air flow blowing mechanism and the forehead support 16, when the apparatus body 13 is disposed at the second height position H2 at which the nozzle projection 21h (air flow blowing nozzle 21b) and the forehead support 16 do not interfere. Note that the third front position FL3 may be set to be different from the second interval i2 between the wall portion 21k of the air flow blowing mechanism and the forehead support 16, without being limited to the embodiment.

The fourth front position FL4 is set from a viewpoint that the wall portion 21k of the air flow blowing mechanism of the intraocular pressure measurement device 20 is prevented from interfering with the forehead support 16, in the case of the eye characteristic measurement mode, basically, as shown in FIG. 7D. That is to say, the third front position FL3 is set to be capable of providing the first interval i1 between the wall portion 21k of the air flow blowing mechanism and the forehead support 16, when the apparatus body 13 is disposed at the second height position H2 at which the nozzle projection 21h (air flow blowing nozzle 21b) and the forehead support 16 do not interfere. Note that the fourth front position FL4 may be set to be different from the first interval i1 between the wall portion 21k of the air flow blowing mechanism and the forehead support 16, without being limited to the embodiment.

When the apparatus body 13 reaches each of the front positions (FL1 to FL4), the front position detector 49 outputs a signal representing the fact to the controller 33 (see FIG. 2). Here, because each of the front positions is set as described above, when the apparatus body 13 (nozzle projection 21h) is positioned between the first front position FL1 and the second front position FL2, the front position detector 49 outputs a signal representing that the apparatus body reaches the second front position FL2 to the controller 33. Similarly, when the apparatus body 13 (the wall portion 21k of the air blowing mechanism) is positioned between the third front position FL3 and the fourth front position FL4, the front position detector 49 outputs a signal showing that the apparatus body reaches the third front position FL3 to the controller 33. In the controller 33, control depending on a situation as described below is basically executed for every signal from the front position detector 49. Here, in a case where the controller 33 acquires the signal (first height position H1) positioned at the height position HL from the front position detector 49, there is a possibility of acquiring from the front position detector 49 a signal that the apparatus body 13 (nozzle projection 21h (air flow blowing nozzle 21b)) reaches the first front position FL1 or the second front position FL2. Here, regardless of the height position, in a case where the front position detector 49 is configured to output the signal, the controller 33 does not execute any control even if it acquires from the front position detector 49 the signal reaching the third front position FL3 or the fourth front position FL4, in the case of the first height position H1. In a case where the controller 33 does not receive the signal positioned at the height position HL from the front position detector 49 (the case of the second height position H2), there is a possibility of acquiring from the front position detector 49 the signal that the apparatus body 13 (the wall portion 21k of the air blowing mechanism) reaches the third front position FL3 or the fourth front position FL4. Here, regardless of the height position, in a case where the front position detector 49 is configured to output the signal, the controller 33 does not execute any control even if it acquires from the front position detector 49 the signal reaching the first front position FL1 or the second front position FL2, in case of the second height position H2.

When the controller 33 acquires the signal that the apparatus body 13 (nozzle projection 21h (air flow blowing nozzle 21b)) reaches the first front position FL1 from the front position detector 49, it stops the forward movement of the apparatus body 13. In other words, in the ophthalmology apparatus 10 (controller 33), if the nozzle projection 21h (air flow blowing nozzle 21b) is in the first height position H1, the inspected eye E side (positive side in the Z-axis direction) rather than the first front position FL1 is set as a movement prohibition area. In the controller 33, control depending on a situation forward moving the apparatus body 13 is executed in accordance with the stop of the forward movement of the apparatus body 13. As the control depending on the situation, for example, it is pointed out to display on the display 14 that the apparatus body cannot be further moved forward, in a case where the apparatus body 13 is forward moved based on the operation executed in the display 14. When the power switch of the ophthalmology apparatus 10 is turned on, the controller 33 determines whether the signal that the apparatus body reaches the first front position FL1 is output from the front position detector 49, before executing the movement of the apparatus body 13. Then, the controller 33 suitably executes the movement of the apparatus body 13, in cases where the controller 33 acquires the signal that the apparatus body is in the height position HL from the height position detector 48 and where the signal that the apparatus body reaches the first front position FL1 is not output from the front position detector 49. In addition, the controller 33 does not execute the forward movement of the apparatus body 13 and executes control depending on a situation, in a case where the signal that the apparatus body reaches the first front position FL1 is output from the front position detector 49. As the control depending on the situation, for example, it is pointed out to display on the display 14 that the apparatus body cannot be further moved forward, in a case where the apparatus body 13 is forward moved based on the operation executed in the display 14.

When the controller 33 acquires from the front position detector 49 the signal that apparatus body (nozzle projection 21h (air flow blowing nozzle 21b)) reaches the second front position FL2, it emits a warning. In other words, in the ophthalmology apparatus 10 (controller 33), if the nozzle projection 21h (air flow blowing nozzle 21b) is in the first height position H1, the inspected eye E side (positive side in the Z-axis direction) rather than the second front position FL2 is set as a movement warning area. The warning is executed by emitting warning sound from a warning sound generator 51 provided on the apparatus body 13 under control of the controller 33, in the embodiment. Here, the warning may be executed by providing a warning lamp on the apparatus body 13 and lighting (blinking) the warning lamp under the control of the controller 33, displaying the warning on the display 14, and providing a vibration generator on the apparatus body 13 and generating vibration by the vibration generator, without being limited to the configuration in the embodiment. The controller 33 may temporarily stop the forward movement of the apparatus body 13 when emitting the warning. In this case, after the movement is temporarily stopped, when the apparatus body 13 is forward moved again, or the operation that the automatic alignment is continued is executed, the forward movement of the apparatus body 13 is permitted again. This is because it depends on user's intentions continuing the operation after the recognition of warning and the confirmation of safety of the user (examiner) to execute operation in which the apparatus body 13 is forward moved or the automatic alignment is continued. As the confirmation of safety, it is pointed out to fail to put the hand H on the forehead support 16, separate the hand H from forehead 16, or let the subject stop putting the hand H on the forehead support 16. Moreover, by previously setting a time temporarily stopping, the forward movement of the apparatus body 13 may be permitted again after the lapse of the set time. Furthermore, in a case where a hand detector which can detect that the hand H is put on the forehead support 16 is provided, as described below, the forward movement of the apparatus body 13 may be permitted again, when detecting that the hand H is separated from the forehead support 16.

Moreover, when the controller 33 acquires the signal that the apparatus body 13 (the wall portion 21k of the air flow blowing mechanism) reaches the third front position FL3, it executes the same control as the case of acquiring the signal of the second front position FL2 and emits the warming. In other words, in the ophthalmology apparatus 10 (controller 33), if the nozzle projection 21h (air flow blowing nozzle 21b) is in the second height position H2, the inspected eye E side (positive side in the Z-axis direction) rather than the third front position FL3 is as the movement warning area. Even in this case, when emitting a warning similar to the case of acquiring the signal of the second front position FL2, the forward movement of the apparatus body 13 may be temporarily stopped.

In addition, the controller 33 acquires the signal that the apparatus body 13 (the wall portion 21k of the air flow blowing mechanism) reaches the fourth front position FL4 from the front position detector 49, it stops the forward movement of the apparatus body 13. In other words, in the ophthalmology apparatus 10 (controller 33), if the nozzle projection 21h (air flow blowing nozzle 21b) is in the second height position H2, the inspected eye E side (positive side in the Z-axis direction) rather than the fourth front position FL4 is set as the movement prohibition area. The controller 33 executes the control depending on the situation forward moving the apparatus body 13 in accordance with the stop of the forward movement of the apparatus body 13. As the control depending on the situation, for example, it is pointed out to display on the display 14 that the apparatus body cannot be further forward moved, in the case of forward moving the apparatus body 13 based on the operation executed on the display 14. When the power switch of the ophthalmology apparatus 10 is turned on, the controller 33 determines whether the signal that the apparatus body reaches the fourth front position FL4 is output from the front position detector 49, before executing the movement of the apparatus body 13. When the controller 33 acquires the signal of the second height position H2 from the height position detector 48 and the signal reaching the fourth front position FL4 is not output from the front position detector 49, the controller suitably executes the movement of the apparatus body 13. In addition, the controller 33 does not execute the forward movement of the apparatus body 13 and executes control depending on a situation, in a case where the signal reaching the fourth front position FL4 is output from the front position detector 49. As the control depending on the situation, for example, it is pointed out to display on the display 14 that the apparatus body cannot be further forward moved, when executing the operation forward moving the apparatus body with the display 14.

The front position detector 49 is provided on the apparatus body 13 in the example shown in FIGS. 7A to 7D, but may be actually provided on the Z-axis driving part 12b of the driver 12 controlling the front-back direction, that is, the position in the Z-axis direction of the apparatus body 13, or on other parts, without being limited to the embodiment. The warning sound generator 51 is provided on the apparatus body 13 in the example shown in FIGS. 7A to 7D, but may be provided on other parts, without being limited to the embodiment, if the examiner or the subject can hear the warning sound.

Next, safety ensuring notifying processing that executes a method of notifying safety ensuring as one embodiment for safety ensuring executed in the controller 33 in moving the apparatus body 13 to the inspected eye E side (positive side in the Z-axis direction) is described with reference to FIG. 9. FIG. 9 is a flow chart illustrating the safety ensuring notifying processing (the method of notifying safety ensuring) executed in the controller 33 in the embodiment. The controller 33 executes the safety ensuring notifying processing (the method of notifying safety ensuring) based on a program stored in the storage provided inside the controller 33, or a storage provided outside the controller 33. Note that the safety ensuring notifying processing (the method of notifying safety ensuring) is to control the movement of the apparatus body 13 to the inspected eye E side (positive side in the Z-axis direction), if movement in the other directions together with this movement is executed, this movement does not influence the movement in the other directions. Here, the movement in the other directions can be controlled by other control (for example, the control by the signal from the height position detector 48 described above)

In the safety ensuring notifying processing (the method of notifying safety ensuring), when the signal that the apparatus body reaches each front position (the first front position FL1, the second front position FL2, the third front position FL3, and the fourth front position FL4) is input in the controller 33 from the front position detector 49, the controller executes notification or limitation to the movement in accordance with the signal. In the safety ensuring notifying processing (the method of notifying safety ensuring), determination processing is executed by combination of the signal whether the apparatus body reaches the height position HL from the height position detector 48, that is, the signal whether the apparatus body positions at the first height position H1 or the second height position H2. Each step (each process) in the flow chart of the safety ensuring notifying processing (the method of notifying safety ensuring) as shown in FIG. 9 is described as follows. The flow chart (the safety ensuring notifying processing (the method of notifying safety ensuring)) is executed while the apparatus body 13 is moved to the inspected eye E (positive side in the Z-axis direction) regardless of the movement by the operation of the examiner (manual movement) or the movement by automation (automatic movement).

In step S1, various information regarding the safety ensuring notifying processing is acquired, and the processing proceeds to step S2. In step S1, the various information used for determination in the safety ensuring notifying processing is acquired. In the embodiment, the various information includes presence or absence of the signal from the height position detector 48, that the apparatus body 13 reaches the height position HL, presence or absence and a type of the signal from the front position detector 49, that the apparatus body 13 reaches each front position (FL1 to FL4), and whether a notification function which is described below is valid.

In step S2, whether the apparatus body 13 reaches the height position HL is determined, following the acquisition of the various information regarding the safety ensuring notifying processing in step S1, and if it is Yes, the processing proceeds to step S3, and if it is No, the processing proceeds to step S8. It is determined in step S2 that the apparatus body 13 reaches the height position HL, that is, the nozzle projection 21h (air flow blowing nozzle 21b) of the intraocular pressure measurement device 20 is positioned at the first height position H1, in the case of receiving from the height position detector 48 the signal representing that the apparatus body 13 reaches the height position HL. In this case, in step S2, because the nozzle projection 21h is in the first height position H1, the processing proceeds to step S3 to use the signal from the front position detector 49, representing that the apparatus body reaches the first front position FL1 of the second front position FL2. In addition, in step S2, if the signal is not received from the height position detector 48, it is determined that the apparatus body 13 does not reach the height position HL, in other words, the nozzle projection 21h (air flow blowing nozzle 21b) of the intraocular pressure measurement device 20 is positioned at the second height position H2. In this case, in step S2, because the nozzle projection 21h is in the second height position H2, the processing proceeds to step S8 to use the signal from the front position detector 49, representing that the apparatus body reaches the third front position FL3 of the fourth front position FL4.

In step S3, whether the notification function is valid is determined, following the determination that the apparatus body 13 reaches the height position HL in step S2, and if it is Yes, the processing proceeds to step S4, and if it is No, the processing proceeds to step S6. In step S3, whether the notification function is valid, that is, the setting of the movement warning area (the inspected eye E side rather than the second front position FL2) is notified is determined. The determination can execute, for example, by displaying icon to select whether validating or invalidating the notification function in the display 14 and determining the operation result of the icon by the examiner. If the controller 33 can determine the result of the selection whether validating or invalidating the notification function by the examiner, other method may be used, without being limited to the embodiment. In addition, as to whether the notification function is valid, if the hand detector detects that the hand H puts on the forehead support 16, the notification function may be valid, if there is no detection, the notification function may be invalid. As the hand detector, for example, a sensor such as a pressure sensitive sensor or electrostatic sensor which can detect that the hand H exists may be provided on a surface of the forehead support 16 facing the nozzle projection 21h (air flow blowing nozzle 21b). As the hand detector, for example, an optical sensor, a camera or the like which can detect that the hand H exists may be provided on a surface of the forehead support 16 facing the nozzle projection 21h (air flow blowing nozzle 21b).

In step S4, whether the apparatus body 13 is in the movement warning area is determined, following the determination that the notification function is valid, in step 3, and if it is Yes, the processing proceeds to step S5, and if it is No, the processing proceeds to step S6. In step S4, whether the signal that the apparatus body 13 (the nozzle projection 21h (air flow blowing nozzle 21b)) reaches the second front position FL2 is acquired from the front position detector 49 is determined. Then, in step S4, if the signal is acquired, it is determined that the apparatus body 13 exists in the movement warning area, and the processing proceeds to step S5, and if the signal is not acquired, it is determined that the apparatus body 13 does not exist in the movement warning area, and the processing proceeds to step S6.

In step S5, the processing proceeds to step S6 by emitting the warning, following the determination that the apparatus body 13 exists in the movement warning area, in step S4. In step S5, the warning is emitted because the notification function is valid and the nozzle projection 21h (air flow blowing nozzle 21b) exists in the movement warning area. In the embodiment, the warning is executed by emitting the warning sound from the warning sound generator 51 as described above. Note that the warning is stopped when it is determined the apparatus body 13 does not reach the height position HL in step S2 repeated thereafter, it is determined that the notification function is not valid in step S3 repeated thereafter, and it is determined that the apparatus body does not exist in movement warning area in step S4 repeated thereafter. Here, the reason including the case where the apparatus body 13 does not reach the height position HL is to set the third front position FL3 or the fourth front position FL4 in a determination standard, as described above. In step S5, when emitting the warning, the forward movement of the apparatus body 13 may be temporarily stopped, as described above.

In step S6, whether the apparatus body 13 reaches the movement prohibition area is determined, and if it is Yes, the processing proceeds to step S7, and if it is No, the processing proceeds to step S13, following the determination that the notification function is not valid in step S3, or the determination that the apparatus body 13 does not exist in the movement warning area in step S4, or emitting the warning in step S5. In step S6, whether the signal that the apparatus body 13 (the nozzle projection 21h (air flow blowing nozzle 21b)) reaches the first front position FL1 is acquired from the front position detector 49 is determined. In addition, in step S6, if the signal is acquired, it is determined that the apparatus body 13 reaches the movement prohibition area, the processing proceeds to step S7, and if the signal is not acquired, it is determined that the apparatus body 13 does not reach the movement prohibition area, and the processing proceeds to step S13.

In step S7, the forward movement of the apparatus body 13 is stopped and the processing proceeds to step S13, following the determination that the apparatus body 13 reaches the movement prohibition area in step S6. In step S7, because the apparatus body reaches the movement prohibition area, the apparatus body 13 is not further forward moved, that is, to the inspected eye E side (positive side in the Z-axis direction) and by stopping the movement, the control depending on the situation is executed, as described above.

In step S8, whether the notification function is valid is determined, and if it is Yes, the processing proceeds to step S9, and if it is No, the processing proceeds to step S11, following the determination that the apparatus body 13 does not reach the height position HL in step S2. In step S8, whether the notification function is valid, that is, whether notifying that the apparatus body is in the movement warning area (inspected eye E side rather than the third front position FL3) is determined. The determination is the same as that in step S3.

In step S9, whether the apparatus body 13 is in the movement warning area is determined, and if it is Yes, the processing proceeds to step S10, and if it is No, the processing proceeds to step S11, following the determination that the notification function is valid in step S8. In step S9, whether the signal that the apparatus body 13 (the wall portion 21k of the air flow blowing mechanism) reaches the third front position FL3 is acquired from the front position detector 49 is determined. In step S9, if the signal is acquired, it is determined that the apparatus body 13 is in the movement warning area and the processing proceeds to step S10, and if the signal is not acquired, it is determined that the apparatus body 13 does not exist in the movement warning area and the processing proceeds to step S11.

In step S10, the processing proceeds to step S11 by emitting the warning, following the determination that the apparatus body 13 is in the movement warning area in step S9. In step S10, the warning is emitted because the notification function is valid and the wall portion 21k of the air flow blowing mechanism is in the movement warning area. The warning is executed by emitting the warning sound from the warning sound generator 51 as described above in the embodiment. Note that the warning is stopped when it is determined the apparatus body 13 reaches the height position HL in step S2 repeated thereafter, it is determined that the notification function is not valid in step S8 repeated thereafter, and it is determined that the apparatus body does not exist in movement warning area in step S9 repeated thereafter. Here, the reason including the case where the apparatus body 13 reaches the height position HL is for setting the first front position FL1 or the second front position FL2 in a determination standard, as described above.

In step S11, whether the apparatus body 13 reaches the movement prohibition area is determined, and if it is Yes, the processing proceeds to step S12, and if it is No, the processing proceeds to step S13, following the determination that the notification function is not valid in step S8, or the determination that the apparatus body 13 does not exist in the movement warning area in step S9, or emitting the warning in step S10. In step S11, whether the signal that the apparatus body 13 (the wall portion 21k of the air flow blowing mechanism) reaches the fourth front position FL4 is acquired from the front position detector 49 is determined. Then, in step S11, if the signal is acquired, it is determined that the apparatus body 13 reaches the movement prohibition area, and the processing proceeds to step S12. In step S11, if the signal is not acquired, it is determined that the apparatus body 13 does not exist in the movement prohibition area, and the processing proceeds to step S13.

In step S12, the forward movement of the apparatus body is stopped and the processing proceeds to step S13, following the determination that the apparatus body 13 reaches the movement prohibition area in step S11. In step S12, because the apparatus body 13 reaches the movement prohibition area, the apparatus body 13 is not moved further forward, that is to the inspected eye E side (positive side in the Z-axis direction) and executes the control depending on the situation in accordance with the stop of the movement, as described above.

In step S13, whether operation stopping the warning is executed is determined, and if it is Yes, the processing proceeds to step S14, and if it is No, the processing proceeds to step S15, following the determination that the apparatus body 13 does not reach the movement prohibition area in step S6, stopping the forward movement of the apparatus body 13 in step S7, the determination that the apparatus body 13 does not reach the movement prohibition area in step S11, or stopping the forward movement of the apparatus body 13 in step S12. In step S13, whether operation stopping the warning emitted in step S5 or step S10 is executed (stop of the warning sound in the embodiment) is determined. The operation stopping the warning can be executed, for example, by displaying a warning stop icon on the display 14 and touching the warning stop icon.

In step S14, the notification function is restrictively invalidated, and the processing proceeds to step S15, following the determination that the operation stopping the warning is executed in step S13. In step S14, because the operation stopping the warning is executed, the notification function is invalid as long as the movement of the apparatus body 13 to the inspected eye E side (positive side in the Z-axis direction) is continued.

In step S15, whether the movement of the apparatus body 13 to the inspected eye E side (positive side in the Z-axis direction) is completed is determined, and if it is Yes, the safety ensuring notifying processing (the method of notifying safety ensuring) is completed, and if it is No, the processing returns to step S1, following the determination that the operation stopping the warning is not executed in step S13, or invalidating restrictively the notification function in step S14. In step S15, the forward movement of the apparatus body 13 is completed, in this situation, the apparatus body 13 cannot be moved to the inspected eye E side. Therefore, whether it is not necessary to execute the safety ensuring notifying processing is determined. As a result, if the movement is completed, the safety ensuring notifying processing is completed, and if the movement is continued, the processing returns to step S1 to continue the safety ensuring notifying processing. Note that the case stopping the forward movement of the apparatus body 13 in step S7 or step S12 is not included in the completion of the forward movement of the apparatus body 13. This is because the movement of the apparatus body is not completed for a scene stopping the forward movement although the signal moving the apparatus body forward is output, in step S7 or step S12.

Next, operation in moving the apparatus body 13 to the inspected eye E side (positive side in the Z-axis direction) in the ophthalmology apparatus 10 is described. It is first assumed that the notification function is valid to be the eye characteristic measurement mode, the apparatus body 13 is moved in the inspected eye E side (positive side in the Z-axis direction), and the apparatus body 13 (nozzle projection 21h) does not yet reach the second front position FL2. Then, in the flow chart shown in FIG. 9, the processing proceeds from step S1 to step S2, thereby it is determined that the nozzle projection 21h (air flow blowing nozzle 21b) is positioned at the first height position H1 by receiving the signal from the height position detector 48 that the apparatus body 13 reaches the height position HL. Then, in the flow chart shown in FIG. 9, the processing proceeds to step S3, step S4, step S6, step S13, and step S15 in order, thereby the movement of the apparatus body 13 to the inspected eye E side (positive side in the Z-axis direction) is executed, without generating any operation.

When the apparatus body 13 (nozzle projection 21h) reaches the second front position FL2 (see FIG. 7B) by the movement, the processing proceeds to step S15, step S1, step S2, step S3, step S4, and step S5 in order, in the flow chart shown in FIG. 9, thereby the warning is emitted. As a result, it is assumed that the operation stopping the warning is executed by the examiner after the examiner recognizes the warning and confirms the safety. Then, the processing proceeds to step S6, step S13, and step S14 in order, in the flow chart shown in FIG. 9, thereby the notification function is restrictively invalidated, the warning is stopped by proceeding to step S15, step S1, step S2, and step S3 in order, in the flow chart shown in FIG. 9. At this time, the movement of the apparatus body 13 to the inspected eye E side (positive side in the Z-axis direction) is continued, and it is assumed that the apparatus body 13 (nozzle projection 21h) reaches the first front position FL1 (see FIG. 7A) through the movement of the apparatus body. Consequently, the movement of the apparatus body 13 to the inspected eye E side (positive side in the Z-axis direction) is stopped by proceeding from step S6 to step S7, in the flow chart shown in FIG. 9. The nozzle projection 21h (the tip) is therefore prevented from interfering with the forehead support 16, without moving the apparatus body 13 from the first front position FL1 to the inspected eye E side (positive side in the Z-axis direction).

It is also assumed that the notification function is valid to become the intraocular pressure measurement mode, the apparatus body 13 is moved in the inspected eye E side (positive side in the Z-axis direction), and the apparatus body 13 (the wall portion 21k of the air flow blowing mechanism) does not yet reach the third front position FL3. Then, in the flow chart shown in FIG. 9, the processing proceeds from step S1 to step S2, thereby it is determined that the nozzle projection 21h (air flow blowing nozzle 21b) is positioned at the second height position H2 by receiving the signal from the height position detector 48 that the apparatus body 13 does not reach the height position HL. Then, in the flow chart shown in FIG. 9, the processing proceeds to step S8, step S9, step S11, step S13, and step S15 in order, thereby the movement of the apparatus body 13 to the inspected eye E side (positive side in the Z-axis direction) is executed, without generating any operation.

When the apparatus body 13 (the wall portion 21k of the air flow blowing mechanism) reaches the third front position FL3 (see FIG. 7C) by the movement, the processing proceeds to step S15, step S1, step S2, step S8, step S9, and step S10 in order, in the flow chart shown in FIG. 9, thereby the warning is emitted. As a result, it is assumed that the operation stopping the warning is executed by the examiner after the examiner recognizes the warning and confirms the safety. Then, the processing proceeds to step S11, step S13, and step S14 in order, in the flow chart shown in FIG. 9, thereby the notification function is restrictively invalidated, the warning is stopped by proceeding to step S15, step S1, step S2, and step S8 in order, in the flow chart shown in FIG. 9. At this time, the movement of the apparatus body 13 to the inspected eye E side (positive side in the Z-axis direction) is continued, and it is assumed that the apparatus body 13 (the wall portion 21k of the air flow blowing mechanism) reaches the fourth front position FL4 (see FIG. 7D) through the movement of the apparatus body. Consequently, the movement of the apparatus body 13 to the inspected eye E side (positive side in the Z-axis direction) is stopped by proceeding from step S11 to step S12, in the flow chart shown in FIG. 9. The wall portion 21k of the air flow blowing mechanism is therefore prevented from interfering with the forehead support 16, without moving the apparatus body 13 from the fourth front position FL4 to the inspected eye E side (positive side in the Z-axis direction).

In the ophthalmology apparatus 10 as one embodiment of the ophthalmology apparatus according to the present invention, the warning is emitted when the apparatus body 13 reaches the second front position FL2 in moving the apparatus body 13 to the inspected eye E side (positive side in the Z-axis direction). The examiner can therefore recognize a possibility that the hand H is interposed between the nozzle projection 21h (air flow blowing nozzle 21b) of the intraocular pressure measurement device 20 of the apparatus body 13 and the forehead support 16. Thereby, the examiner confirms the safety from failing to put on the hand H with the forehead support 16, separating the hand H from the forehead support 16, stopping to put the hand H on the forehead support 16, and so on, and hence the hand H is prevented from being interposed between the nozzle projection 21h (air flow blowing nozzle 21b) and the forehead support 16.

Moreover, in the ophthalmology apparatus 10, when the apparatus body 13 reaches the first front position FL1 in moving the apparatus body 13 to the inspected eye E side (positive side in the Z-axis direction), the movement of the apparatus body 13 to the inspected eye E side (positive side in the Z-axis direction) is stopped. Therefore, in the ophthalmology apparatus 10, the nozzle projection 21h (air flow blowing nozzle 21b) of the intraocular pressure measurement device 20 can be certainly prevented from interfering with the forehead support 16.

Furthermore, in the ophthalmology apparatus 10, even if the apparatus body 13 reaches the second front position FL2, the movement of the apparatus body 13 to the inspected eye E side (positive side in the Z-axis direction rather than the second front position FL2) is not completely prohibited. As a result, in the ophthalmology apparatus 10, the hand H is prevented from being interposed between the nozzle projection 21h (air flow blowing nozzle 21b) and the forehead support 16, a range capable of moving the apparatus body 13 can be prevented from narrowing, and usability can be improved.

In the ophthalmology apparatus 10, when the apparatus body 13 reaches the second front position FL2, the second interval i2 is set between the nozzle projection 21h (air flow blowing nozzle 21b) of the intraocular pressure measurement device 20 and the forehead support 16. The second interval i2 is set from the viewpoint preventing the hand H positioned between the tip of the nozzle projection 21h (air flow blowing nozzle 21b) and the forehead support 16 from being interposed. Therefore, in the ophthalmology apparatus 10, the hand H is certainly prevented from being interposed between the nozzle projection 21h (air flow blowing nozzle 21b) and the forehead support 16.

In the ophthalmology apparatus 10, when the apparatus body 13 reaches the first front position FL1, the first interval i1 is set between the nozzle projection 21h (air flow blowing nozzle 21b) of the intraocular pressure measurement device 20 and the forehead support 16. The first interval i1 is set to be the value as small as possible on the presumption that the interference between the tip of the nozzle projection 21h and the forehead support 16 can be certainly prevented. In the ophthalmology apparatus 10, it is therefore possible to certainly prevent the interference between the nozzle projection 21h (air flow blowing nozzle 21b) and the forehead support 16 and the reduction of the range that can move the apparatus body 13.

In the ophthalmology apparatus 10, when the notification function is invalidated, the usability can be improved because the warning is not emitted even if the apparatus body 13 reaches the second front position FL2. In other words, this is because the warning is troublesome for executing the measurement after confirming not to put the hand H on the forehead support 16 even if the hand H is not interposed between the nozzle projection 21h (air flow blowing nozzle 21b) and the forehead support 16.

In the ophthalmology apparatus 10, because the detection is made that the apparatus body 13 reaches each of the front positions (first front position FL1 and the second front position FL2), it is possible to certainly detect that the apparatus body is reached each front position with a simple configuration.

In the ophthalmology apparatus 10, even to the wall portion 21k of the air flow blowing mechanism, the third front position FL3 and the fourth front position FL4 are set, and the control similar to that in the nozzle projection 21h (air flow blowing nozzle 21b) is executed. As a result, in the ophthalmology apparatus 10, it is possible to secure further safety and improve the usability.

In the ophthalmology apparatus 10, by providing the hand detector which can detect that the hand H is put on the forehead support 16, if the hand detector detects that the hand H is put on the forehead support 16, the notification function can be validated, if the detection does not exist, the notification function can be invalidated. Therefore, in the ophthalmology apparatus 10, it is possible to emit the warning when the apparatus body 13 reaches the second front position FL2 only if the hand H is actually put on the forehead support 16, without being set by the examiner in particular. Thereby, in the ophthalmology apparatus 10, the usability can be further improved.

In the ophthalmology apparatus 10, it is possible to temporarily stop the forward movement of the apparatus body 13 when the apparatus body 13 reaches the second front position FL2 and the warning is emitted. Therefore, in the ophthalmology apparatus 10, even if the hand H is put on the forehead support 16, it is possible to execute with allowance the confirmation of the safety such as letting the examiner separate the hand H from the forehead support 16, or letting the examiner stop to put the hand H on the forehead support 16. Thereby, in the ophthalmology apparatus 10, the usability can be further improved.

In the ophthalmology apparatus 10, the forward movement of the apparatus body 13 is temporarily stopped when the apparatus body 13 reaches the second front position FL2 and the warning is emitted. When the operation to forward move the apparatus body 13 is executed again or the operation to continue the automatic alignment is executed, the forward movement of the apparatus body 13 can be permitted again. As a result, in the ophthalmology apparatus 10, because the apparatus body 13 is forward moved again by executing the operation described above after confirming the safety, it is possible to move the apparatus body 13 by further certainly ensuring the safety. Thereby, in the ophthalmology apparatus 10, the usability can be further improved.

In the ophthalmology apparatus 10, the forward movement of the apparatus body 13 is temporarily stopped when the apparatus body 13 reaches the second front position FL2 and the warning is emitted. By previously setting a temporarily stopping time, after the set time passes, the forward movement of the apparatus body 13 can be permitted again. Therefore, in the ophthalmology apparatus 10, because the apparatus body 13 is forward moved again, after confirming the safety, without executing any operation, it is possible to move the apparatus body 13 rapidly while ensuring the safety. Thereby, in the ophthalmology apparatus 10, the usability can be further improved.

In the ophthalmology apparatus 10, the forward movement of the apparatus body 13 is temporarily stopped when the apparatus body 13 reaches the second front position FL2 and the warning is emitted. In addition, when the hand detector that can detect that the hand H is put on the forehead support 16 is provided as described above and the hand H is put on the forehead support 16, the forward movement of the apparatus body 13 can be stopped and the forward movement of the apparatus body 13 can be permitted again when the hand H separates from the forehead support 16. Therefore, in the ophthalmology apparatus 10, the forward movement of the apparatus body 13 is temporarily stopped when the apparatus body 13 reaches the second front position FL2 only if the hand H is actually put on the forehead support 16, without being set by the examiner in particular, and the apparatus body 13 can be forward moved rapidly when the hand H separates from the forehead support 16. Thereby, in the ophthalmology apparatus 10, the usability can be further improved.

Accordingly, in the ophthalmology apparatus 10 as one embodiment of the ophthalmology apparatus according to the present invention, the intraocular pressure measurement device 20 as the second measurer is prevented from interfering with the forehead support 16 and the hand H is prevented from being interposed in the intraocular pressure measurement device 20 as the second measurer.

To solve the problem in that, because the second measurer (tip end thereof) upward and forward positioned approximates the forehead support positioned above the inspected eye when forward moving the first measurer in measuring the inspected eye by use of the first measurer which is downward positioned, the second measurer (tip end thereof) has a possibility interfering with the forehead support depending on position setting or a quantity of movement, or interposing the hand H if the hand is put on the forehead support even if the interference does not occur, the ophthalmology apparatus includes the first measurer set at the first setting working distance to measure the inspected eye of the subject, the second measurer set at the second setting working distance shorter than the first setting working distance to measure the inspected eye and integrally provided above the first measurer, the apparatus body on which the first measurer and the second measurer are provided and which is movable relative to the base, the driver that moves the apparatus body relative to the base, the forehead support provided on the base to support the forehead of the subject, and the controller that controls the first measurer, the second measurer, and the driver. The controller is configured to detect the first front position in the apparatus body, in which the distance between the second measurer and the forehead support is set as the first interval and the second front position in the apparatus body, in which the distance between the second measurer and the forehead support is set as the second interval larger than the first interval. The controller emits the warning when the apparatus body reaches the second front position in moving the apparatus body to a forehead support side and stops the movement of the apparatus body to the forehead support side when the apparatus body reaches the first front position. With this configuration, the second measurer is prevented from interfering with the forehead support and the hand put on the forehead support can be prevented from being interposed by the second measurer.

In addition to the above configuration, the second interval is set to prevent the hand put between the second measurer and the forehead support from being interposed. With the configuration, the hand can be further certainly prevented from being interposed between the second measurer and the forehead support from being interposed.

In addition to the above configuration, the first interval is set to be the small value, while preventing the second measurer and the forehead support from interfering. With the configuration, the interference between the second measurer and the forehead support can be certainly prevented and the movable range of the apparatus body can be prevented from reducing.

In addition to the above configuration, the controller does not emit the warning even if the apparatus body reaches the second front position when the notification function that emits the warning is invalidated. With the configuration, the usability can be improved.

In addition to the above configuration, the hand detector which detects that the hand is put on the forehead support is further provided, and the controller determines that the notification function is invalidated when the hand detector detects that the hand is not put on the forehead support. With the configuration, it is possible to emit the warning when the apparatus body reaches the second front position only if the hand is actually put on the forehead support without being set by the examiner in particular. The usability can be further improved.

In addition to the above configuration, when the apparatus body reaches the second front position and the controller emits the warning, the controller temporarily stops the movement of the apparatus body to the forehead support side. With the configuration, even if the hand is put on the forehead support, it is possible to execute with allowance the confirmation of the safety such as letting the examiner separate the hand H from the forehead support, or letting the examiner stop to put the hand on the forehead support and improve the usability.

In addition to the above configuration, the front position detector to detect that the apparatus body is disposed on the first front position or the second front position and output the detection result to the controller is further provided. With the configuration, it is possible to certainly detect that the apparatus body reaches each front position with a simple configuration.

In addition to the above configuration, the second measurer includes the detection optical system that detects the position of the inspected eye in the direction toward the inspected eye by receiving reflection light, and the controller detects that the apparatus body reaches the second front position by determining that the hand put on the forehead support is approaching based on the quantity of the reflection light in the detection optical system. With the configuration, it is detected at a time that the apparatus body reaches the second front position and that the hand is put on the forehead support. The usability can be therefore further improved. In addition, because the detection optical system is used for the measurement by the second measurer, the configuration makes it possible to form the ophthalmology apparatus with a simple configuration and can be easily applied to an existing device.

In addition to the above configuration, reflectivity of the surface of the forehead support facing the second measurer is set to be different from reflectivity of the hand. With the configuration, it can be further adequately determined that the hand is put on the forehead support.

In addition to the above configuration, the second measurer includes the detection optical system that detects the position of the inspected eye in the direction toward the inspected eye by receiving reflection light, reflectivity of the surface of the forehead support facing the second measurer is set to be smaller than reflectivity of the hand, and the controller detects that the apparatus body reaches the second front position when the quantity of reflection light received on the detection optical system exceeds a detection threshold set to detect that the hand is approaching. With the configuration, it is detected at a time that the apparatus body reaches the second front position and that the hand is put on the forehead support. The usability can be therefore further improved. In addition, because the detection optical system is used for the measurement by the second measurer, the configuration makes it possible to form the ophthalmology apparatus with a simple configuration and can be easily applied to an existing device.

In addition to the above configuration, the second measurer includes the observation optical system that acquires the image of the anterior ocular segment in the direction toward the inspected eye, and the controller is configured to grip existence of the hand put on the forehead support based on the image of the anterior ocular segment acquired in the observation optical system, and detect that the apparatus body reaches the second front position by determining that the hand put on the forehead support is approaching. With the configuration, it is detected at a time that the apparatus body reaches the second front position and that the hand is put on the forehead support. The usability can be therefore further improved. In addition, because the detection optical system is used for the measurement by the second measurer, the configuration makes it possible to form the ophthalmology apparatus with a simple configuration and can be easily applied to an existing device.

Here, in the embodiment as described above, although the ophthalmology apparatus 10 as the ophthalmology apparatus according to the present invention, the ophthalmology apparatus may be configured to include the first measurer set at the first setting working distance to measure the inspected eye of the subject, the second measurer set at the second setting working distance shorter than the first setting working distance to measure the inspected eye and integrally provided above the first measurer, the apparatus body on which the first measurer and the second measurer are provided and which is movable relative to the base, the driver that moves the apparatus body relative to the base, the forehead support provided on the base to support the forehead of the subject, and the controller that controls the first measurer, the second measurer, and the driver, the controller is configured to detect the first front position in the apparatus body, in which the distance between the second measurer and the forehead support is set as the first interval and the second front position in the apparatus body, in which the distance between the second measurer and the forehead support is set at the second interval larger than the first interval, and the controller emits the warning when the apparatus body reaches the second front position in moving the apparatus body to the forehead support side and stops the movement of the apparatus body to the forehead support side when the apparatus body reaches the first front position. The ophthalmology apparatus is not limited to the configuration in the embodiment.

In the above-described embodiment, the controller 33 is configured to determine the height position of the apparatus body 13 based on the presence or the absence of the signal from the height position detector 48 and determine the position of the apparatus body 13 (nozzle projection 21h (air flow blowing nozzle 21b)) in the Z-axis direction based on the type and the presence or absence of the signal from the front position detector 49. However, the controller 33 may be able to determine either the height position (either the first height position H1 or the second height position H2), or in the Z-axis direction, the front positions (the first front position FL1, the second front position FL2, the third front position FL3, and the fourth front position FL4) of the apparatus body 13 (nozzle projection 21h (air flow blowing nozzle 21b)), and is not limited to the embodiment described above. One example of other configurations is described as follows. A case where the drive sources of the Y-axis driving part 12a, the Z-axis driving part 12b, and the X-axis driving part 12c of the driver 12 are controlled using a pulse number of a pulse motor, the controller 33 can determine each position in the X, Y, and Z directions and store by counting a pulse number from the standard position in each of the X, Y, and Z directions and storing the counted number. The controller 33 stores the height position HL and the front positions (FL1 to FL4) together using the function, thereby enabling to determine which position the moving apparatus body 13 (nozzle projection 21h (air flow blowing nozzle 21b)) exists at.

Further, in the above-described embodiment, the controller 33 detects that the apparatus body 13 reaches the second front position FL2 by acquiring the signal reaching the second front position from the front position detector 49. However, the controller 33 may use the detection optical system (the Z alignment index projecting optical system 25, the Z alignment detecting optical system 26, and the Z alignment detection corrector 32 (see FIG. 2)) capable of detecting the position of the inspected eye E in the intraocular pressure measurement device 20 as the second measurer in the Z-axis direction (the direction toward the inspected eye E). This is because the forehead support 16 is positioned on the optical axis O1 of the intraocular pressure measurement device 20 since the determination of the presence or the absence of the reaching the second front position FL2 is executed in the case where the apparatus body 13 is in the first height position H1 capable of interfering the nozzle projection 21h (air flow blowing nozzle 21b) and the forehead support 16.

In the detection optical system, by lighting the light source for Z alignment 25a of the Z alignment index projecting optical system 25, the parallel light flux for alignment in the Z-axis direction is projected on the optical axis of the Z alignment index projecting optical system 25. When the cornea Ec of the inspected eye E exists on the optical axis of the Z alignment index projecting optical system 25, the parallel light flux for alignment in the Z-axis direction is projected on the cornea Ec, and the reflection light flux reflected on the cornea Ec is received on the sensor 26c of the Z alignment detecting optical system 26. The detection signal cannot be therefore output, in the detection optical system, if the cornea Ec of the inspected eye E does not exist on the optical axis. If the cornea Ec of the inspected eye E exists on the optical axis, the detection signal can be output and the inspected eye E (cornea Ec) is positioned in the detectable range. From such a configuration, when the forehead support 16 is positioned on the optical axis O1 of the intraocular pressure measurement device 20, if the hand H is put on the forehead support, the reflection light flux that the foregoing alignment index light is reflected on the hand H is acquired by the sensor 26c (see FIG. 10A). If the hand H is not put on the forehead support, the reflection light flux that the alignment index light is reflected on the forehead support 16 is acquired by the sensor 26c (see FIG. 10B).

Here, because the cornea Ec is a state close to a mirror surface, when the cornea Ec exists on the optical axis of the Z alignment index projecting optical system 25, a slit-shaped image is formed on the sensor 26c. On the contrary, the hand H (forehead support 16) is not a state close to the mirror surface and scatters and reflects the parallel light flux from the Z alignment index projecting optical system 25. When the hand H (forehead support 16) therefore exists on the optical axis of the Z alignment index projecting optical system 25, the image of the hand H (forehead support 16) (a part thereof) is not formed on the sensor 26c. However, light receiving in the sensor becomes bright as a whole by receiving the scattered light on the sensor 26c. In the detection optical system (sensor 26c), the brightness increases as the hand H (forehead support 16) approaches the intraocular pressure measurement device 20, as viewed in the direction of the optical axis O1, that is, the receiving reflection light quantity increases. Note that, in the detection optical system, it is possible to easily determine because there is not the reflection light quantity when nothing exists on the optical axis of the Z alignment index projecting optical system 25.

Here, because the forehead support 16 exists in a predetermined position as viewed in the direction of the optical axis O1 and reflectivity thereof is also known, the reflection light quantity received on the detection optical system (the Z alignment detecting optical system 26 (the sensor 26c)) is predetermined. The hand H put on the forehead support 16 is closer to the intraocular pressure measurement device 20 than the forehead support 16 as viewed in the direction of the optical axis O1. The reflection light quantity received on the detection optical system therefore increases as compared to the reflection light quantity from the forehead support 16. Accordingly, in the detection optical system, it is possible to set the detection threshold in consideration of the both reflection light quantities and detect that the hand H exists between the intraocular pressure measurement device and the forehead support 16 by the reflection light quantity exceeding the detection threshold. By setting the detection threshold to a value corresponding to the reflection light quantity from the hand H existing in a position before the hand is interposed between the nozzle projection 21h (air flow blowing nozzle 21b) of the intraocular pressure measurement device 20 and the forehead support 16, it is possible to detect that the apparatus body 13 (nozzle projection 21h) reaches the second front position FL2 by the reflection light quantity exceeding the detection threshold. The second front position FL2 in this case is the same as the foregoing embodiment in that the hand is prevented from being interposed between the nozzle projection 21h (air flow blowing nozzle 21b) of the intraocular pressure measurement device 20 and the forehead support 16. However, the second front position is not necessarily the completely equal interval to the second interval i2.

From this, the controller 33 can detect both the apparatus body 13 which has been reached the second front position FL2 and the hand H which has been put on the forehead support 16 at a time by detecting that the reflection light quantity exceeds the detection threshold by use of the detection optical system. In this way, when it is detected that the reflection light quantity exceeds the detection threshold, in other words, the apparatus body 13 reaches the second front position FL2, the warning is emitted, thereby improving the usability. In addition, because the Z alignment detecting optical system 26 provided for the measurement by the intraocular pressure measurement device 20 is used, the configuration makes it possible to form the ophthalmology apparatus with a simple configuration and can be easily applied to an existing device.

Here, as described above, if the detection optical system in the intraocular pressure measurement device 20 as the second measurer is used and if a difference between the reflection light quantity from the forehead support 16 and the reflection light quantity from the hand H is not clear and adequate detection is difficult, the reflectivity of the surface of the forehead support 16 facing the nozzle projection 21h (air flow blowing nozzle 21b), to the alignment index light may be set to be different from the reflectivity of the hand H to the alignment index light. As this example, it is pointed that the reflectivity of the surface of the forehead support 16 facing the nozzle projection 21h (air flow blowing nozzle 21b) is set to be very low. With this configuration, if nothing exists on the optical axis of the Z alignment index projecting optical system 25 and the forehead support 16 exists on the optical axis, it is possible to certainly prevent the exceeding of the set detection threshold as described above, because the reflection light quantity received on the detection optical system is very small. By detecting that the reflection light quantity received on the detection optical system exceeds the detection threshold, it is possible to certainly detect that the apparatus body 13 reaches the second front position FL2 by the apparatus body approaching the hand H put on the forehead support 16. As other example of using different reflectivity, it is pointed that the reflectivity of the surface of the forehead support 16 facing the nozzle projection 21h (air flow blowing nozzle 21b) is set to be high. With this configuration, it is possible to determine that the hand H is not put on the forehead support 16, in the case of a large quantity of the reflection light and the hand H is put on the forehead support 16, in the case of a small quantity of the reflection light. The setting of the reflectivity can be easily executed by painting a part showing the reflectivity or attaching a seal to the part.

In the above-described embodiment, the controller 33 acquires the signal that the apparatus body reaches the second front position FL2, from the front position detector 49, and thereby detects that the apparatus body 13 reaches the second front position FL2. However, the controller 33 may use the anterior ocular segment observing optical system 21 of the intraocular pressure measurement device 20 as the second measurer. This is because the forehead support 16 is positioned on the optical axis O1 of the intraocular pressure measurement device 20 since the determination of the presence or the absence of reaching the second front position FL2 is executed if the apparatus body 13 is in the first height position H1 capable of interfering the nozzle projection 21h (air flow blowing nozzle 21b) and the forehead support 16. In this case, the controller analyzes the image (data thereof) acquired in the anterior ocular segment observing optical system 21 (CCD camera 21i thereof) of the intraocular pressure measurement device 20 as the second measurer, and thereby can determine whether the hand H is put on the forehead support 16, or the hand is not put on the forehead support 16. When it is determined that the hand H is put on the forehead support 16, if it is determined that the hand H exists in a position before the hand is interposed between the nozzle projection 21h (air flow blowing nozzle 21b) of the intraocular pressure measurement device 20 and the forehead support 16, it is determined that the apparatus body 13 reaches the second front position FL2. Such a determination can be executed by analyzing, for example, a dimension of the forehead support 16 on the image (data thereof). Thereby, it is possible to detect both the apparatus body 13 which is reached the second front position FL2 and the hand H which is put on the forehead support 16 at a time. In this way, if it is detected that the apparatus body has been reached the second front position FL2, the warning is emitted, thereby further improving the usability. In addition, because the anterior ocular segment observing optical system 21 provided for the measurement by the intraocular pressure measurement device 20 is used, and the configuration makes it possible to form the ophthalmology apparatus with a simple configuration and can be easily applied to an existing device. Note that the configuration using the anterior ocular segment observing optical system 21 can be used together with the configuration using the detection optical system of the intraocular pressure measurement device 20. In this case, the warning may be emitted in either one of the anterior ocular segment observing optical system and the detection optical system, when it is detected that the hand H is put on the forehead support 16 and the apparatus body 13 reaches the second front position FL2.

In the above-described embodiment, although the intraocular pressure measurement device 20 as the second measurer is provided, an intraocular pressure measurement device different from the intraocular pressure measurement device in an optical configuration, an arrangement of each optical member, and a measurement principle, or a pachymeter that measures a thickness of the cornea (cornea thickness measurement) may be used, without being limited to the embodiment as described above, provided that the second measurer is set at the second setting working distance d2 of a smaller value than that of the first setting working distance d1.

In the above-described embodiment, although the eye characteristic measurement device 40 as the first measurer is provided, other eye characteristic measurement device different from the eye characteristic measurement device in an optical configuration, an arrangement of each optical member, and a measurement principle, or measurement content (type) may be used, without being limited to the embodiment as described above, provided that the other device receives the reflection light on the inspected eye E and measures an optical characteristic of the inspected eye E.

Although the ophthalmology apparatus of the present invention has been described based on the embodiment, the change and the addition of the design in the embodiment should be permitted as long as they do not depart from the gist of the present invention, without being limited to the embodiment as to concrete configurations.

What is claimed is:

1. An ophthalmology apparatus comprising:
a first measurer set at a first setting working distance to measure an inspected eye of a subject;
a second measurer set at a second setting working distance shorter than the first setting working distance to measure the inspected eye and integrally provided above the first measurer;
an apparatus body on which the first measurer and the second measurer are provided and which is movable relative to a base;
a driver that moves the apparatus body relative to the base;
a forehead support provided on the base to support a forehead of the subject; and
a controller that controls the first measurer, the second measurer, and the driver,
wherein the controller is configured to detect a first front position in the apparatus body, in which a distance between the second measurer and the forehead support is set as a first interval and a second front position in the apparatus body, in which a distance between the second measurer and the forehead support is set as a second interval larger than the first interval, and
wherein the controller emits a warning when the apparatus body reaches the second front position in moving the apparatus body to a forehead support side and stops the movement of the apparatus body to the forehead support side when the apparatus body reaches the first front position.

2. An ophthalmology apparatus comprising:
a first measurer set at a first setting working distance to measure an inspected eye of a subject;

a second measurer set at a second setting working distance shorter than the first setting working distance to measure the inspected eye and integrally provided above the first measurer;
an apparatus body on which the first measurer and the second measurer are provided and which is movable relative to a base;
a driver that moves the apparatus body relative to the base;
a forehead support provided on the base to support a forehead of the subject; and
a controller that controls the first measurer, the second measurer, and the driver,
wherein the controller is configured to detect a first front position in the apparatus body, in which a distance between the second measurer and the forehead support is set as a first interval and a second front position in the apparatus body, in which a distance between the second measurer and the forehead support is set as a second interval larger than the first interval,
wherein the controller emits a warning when the apparatus body reaches the second front position in moving the apparatus body to a forehead support side and stops the movement of the apparatus body to the forehead support side when the apparatus body reaches the first front position, and
wherein the second interval is set to prevent a hand put between the second measurer and the forehead support from being interposed.

3. An ophthalmology apparatus comprising:
a first measurer set at a first setting working distance to measure an inspected eye of a subject;
a second measurer set at a second setting working distance shorter than the first setting working distance to measure the inspected eye and integrally provided above the first measurer;
an apparatus body on which the first measurer and the second measurer are provided and which is movable relative to a base;
a driver that moves the apparatus body relative to the base;
a forehead support provided on the base to support a forehead of the subject; and
a controller that controls the first measurer, the second measurer, and the driver,
wherein the controller is configured to detect a first front position in the apparatus body, in which a distance between the second measurer and the forehead support is set as a first interval and a second front position in the apparatus body, in which a distance between the second measurer and the forehead support is set as a second interval larger than the first interval,
wherein the controller emits a warning when the apparatus body reaches the second front position in moving the apparatus body to a forehead support side and stops the movement of the apparatus body to the forehead support side when the apparatus body reaches the first front position, and
wherein the first interval is set to be a small value, while preventing the second measurer and the forehead support from interfering.

4. The ophthalmology apparatus according to claim 1, wherein the controller does not emit the warning even if the apparatus body reaches the second front position when a notification function that emits the warning is invalidated.

5. The ophthalmology apparatus according to claim 4, further comprising a hand detector which detects that the hand is put on the forehead support,
wherein the controller determines that the notification function is invalidated when the hand detector detects that the hand is not put on the forehead support.

6. The ophthalmology apparatus according to claim 1, wherein when the apparatus body reaches the second front position and the controller emits the warning, the controller temporarily stops the movement of the apparatus body to the forehead support side.

7. The ophthalmology apparatus according to claim 1, further comprising a front position detector configured to detect that the apparatus body is disposed on the first front position or the second front position and output a detection result to the controller.

8. The ophthalmology apparatus according to claim 1, wherein the second measurer includes a detection optical system that detects a position of the inspected eye in a direction toward the inspected eye by receiving reflection light, and
the controller detects that the apparatus body reaches the second front position by determining that the hand put on the forehead support is approaching based on a quantity of the reflection light in the detection optical system.

9. The ophthalmology apparatus according to claim 8, wherein reflectivity of a surface of the forehead support facing the second measurer is set to be different from reflectivity of the hand.

10. The ophthalmology apparatus according to claim 1, wherein the second measurer includes a detection optical system that detects a position of the inspected eye in a direction toward the inspected eye by receiving reflection light,
reflectivity of a surface of the forehead support facing the second measurer is set to be smaller than reflectivity of the hand, and
the controller detects that the apparatus body reaches the second front position when a quantity of reflection light received on the detection optical system exceeds a detection threshold set to detect that the hand is approaching.

11. The ophthalmology apparatus according to claim 1, wherein the second measurer includes an observation optical system that acquires an image of an anterior ocular segment in a direction toward the inspected eye, and
the controller is configured to grip existence of the hand put on the forehead support based on the image of the anterior ocular segment acquired in the observation optical system, and detects that the apparatus body reaches the second front position by determining that the hand put on the forehead support is approaching.

12. The ophthalmology apparatus according to claim 8, wherein the second measurer includes an observation optical system that acquires an image of an anterior ocular segment in a direction toward the inspected eye, and
the controller is configured to grip existence of the hand put on the forehead support based on the image of the anterior ocular segment acquired in the observation optical system, and detects that the apparatus body reaches the second front position by determining that the hand put on the forehead support is approaching.

* * * * *